United States Patent [19]

Temple, Jr.

[11] Patent Number: 4,489,078
[45] Date of Patent: Dec. 18, 1984

[54] DIAZAHETEROCYCLOPURINES USED AS ANTI-BRONCHO SPASMATICS AND VASODILATORS

[75] Inventor: Davis L. Temple, Jr., Evansville, Ind.

[73] Assignee: Mead Johnson & Company, Evansville, Ind.

[21] Appl. No.: 423,888

[22] Filed: Sep. 27, 1982

Related U.S. Application Data

[60] Division of Ser. No. 209,791, Nov. 24, 1980, Pat. No. 4,366,156, which is a division of Ser. No. 017,771, Mar. 5, 1979, Pat. No. 4,298,734, which is a continuation-in-part of Ser. No. 869,203, Jan. 13, 1978, abandoned, which is a continuation-in-part of Ser. No. 768,291, Feb. 14, 1977, abandoned.

[51] Int. Cl.³ .......................................... A61K 31/505
[52] U.S. Cl. .................................. 424/251; 260/243.3
[58] Field of Search ........................................ 424/251

*Primary Examiner*—Glennon H. Hollrah
*Assistant Examiner*—D. B. Springer
*Attorney, Agent, or Firm*—Robert H. Uloth; Richard P. Ryan

[57] ABSTRACT

Imidazopyrimidinones and other diazaheterocyclopyrimidinones having an additional fused imidazole or triazole ring have utility as bronchodilators, mediator release inhibitors, phosphodiesterase inhibitors, and peripheral vasodilators. They are orally active and useful in the prophylaxis and treatment of asthma. A preferred compound is 4-[(4-chlorophenyl)methyl]-6,7-dihydro-3H-imidazo[1,2-a]purin-9(4H)-one.

32 Claims, No Drawings

DIAZAHETEROCYCLOPURINES USED AS ANTI-BRONCHO SPASMATICS AND VASODILATORS

REFERENCE TO RELATED APPLICATION

This application is a division of co-pending application Ser. No. 209,791 filed Nov. 24, 1980 (now U.S. Pat. No. 4,366,156) which is a division of Ser. No. 017,771 filed Mar. 5, 1979 (now U.S. Pat. No. 4,298,734) which is a continuation-in-part of Ser. No. 869,203 filed Jan. 13, 1978 and abandoned Mar. 17, 1979, which in turn is a continuation-in-part of Ser. No. 768,291 filed Feb. 14, 1977 and abandoned Oct. 13, 1978.

FIELD OF THE INVENTION

The invention is concerned with aminopyrimidine compounds having a fused heterocyclic ring on the pyrimidine ring. It is also concerned with drug, bioaffecting and body treating compositions containing these heterocyclic pyrimidine compounds.

DESCRIPTION OF THE PRIOR ART

Hardtmann, U.S. Pat. No. 3,833,588 patented Sept. 3, 1974. Imidazo[2,1-b]quinazolones, pyrimido[2,1-b]quinazolones having an alkenyl, alkynyl, or cyanoalkyl group attached to the central ring nitrogen atom are shown to have anti-inflammatory and bronchodilator activity.

Hardtmann, U.S. Pat. No. 3,859,289 patented Jan. 7, 1975. Imidazo[1,2-a]pyrido-[2,3-d]pyrimidinones, diazepino[1,2-a]pyrido[2,3-d]pyrimidinones, pyrido[2,3-d]pyrimido[2,3-d]pyrimidinones are bronchodilators or hypotensive agents.

Hardtmann, U.S. Pat. No. 3,894,022 patented July 8, 1975. Diazaheterocyclo[2,1-b]quinazolones of the type described in U.S. Pat. No. 3,833,588 which is referred to above, but which have a fourth fused heterocyclic ring bridging the ring nitrogen atoms at the 1-10, 1-11, or 1-12 positions are anti-inflammatory, analgesic, and immunosuppressant agents.

Hardtmann, U.S. Pat. No. 3,969,506 patented July 13, 1976. Diazaheterocycloquinazolones of the structural types disclosed in U.S. Pat. No. 3,833,588 referred to above but which differ from those compounds in having an alkyl or aralkyl group, the latter may be ring substituted, attached to the central ring nitrogen atom, have bronchodilator activity.

Hardtmann, U.S. Pat. No. 3,982,000 patented Sept. 21, 1976. Diazaheterocycloquinazolones similar to those of U.S. Pat. No. 3,969,506 referred to above but which differ from those compounds in having from 1 to 3 lower alkyl groups carbon attached to the heterocyclo fused ring have bronchodilator activity.

Hardtmann, et al., J. Med. Chem. 18, 447–453 (1975). This article deals with substantially the same subject matter as U.S. Pat. Nos. 3,833,588, 3,969,506, and 3,982,000 which are cited above.

SUMMARY OF THE INVENTION

The compounds of the present invention are shown by Formulas XI, XII, XIV, XV, XVI, XVII, XVIII, XX, XXII, and XXIII. Formulas I and II refer to compounds included within the enlarged group of compounds covered by Formulas XX and XI, respectively.

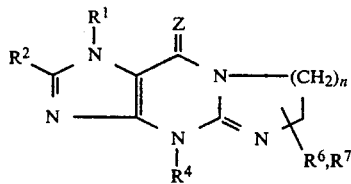

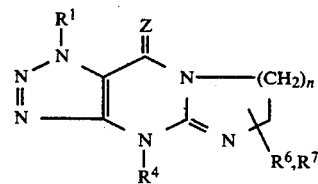

In these formulas, $R^1$ is hydrogen or the group A wherein A is a lower alkyl or lower alkenyl group each having up to 8 carbon atoms, pyridylmethyl, aralkyl having 7 to 12 carbon atoms, substituted aralkyl having 7 to 12 carbon atoms, aryloxyalkyl having 8 to 12 carbon atoms, or substituted aryloxyalkyl having 8 to 12 carbon atoms wherein each of said substituted aralkyl, and substituted aryloxyalkyl groups contain 1 or 2 substituents selected from halogen, alkoxy, and alkyl, and each of said alkoxy and alkyl groups contains up to 6 carbon atoms. $R^2$ is hydrogen, trifluoromethyl, halogen (including fluorine, chlorine, bromine, iodine), or lower alkyl wherein each of said lower alkyl groups has up to 8 carbon atoms. When $R^1$ is other than hydrogen, $R^2$ may additionally be azido, cyano, amino, lower alkyl amino or dilower alkylamino, each of the latter having up to 8 carbon atoms. $R^4$ is hydrogen, lower alkyl having up to 8 carbon atoms, 2-pyridylmethyl, 3-pyridylmethyl, 4-pyridylmethyl, lower alkanoyl or lower alkenoyl each having up to 8 carbon atoms, aroyl having 7 to 10 carbon atoms, substituted aroyl having 7 to 12 carbon atoms, aralkyl having 7 to 12 carbon atoms, substituted aralkyl having 7 to 12 carbon atoms, aryloxyalkyl having 8 to 12 carbon atoms, or substituted aryloxyalkyl having 8 to 12 carbon atoms wherein each of said substituted aroyl, substituted aralkyl, and substituted aryloxyalkyl groups contains one or two ring substituents selected from halo, alkoxy, and alkyl wherein each of said alkoxy and alkyl groups contains up to 6 carbon atoms. Preferred bronchodilator compounds are those in which $R^4$ is substituted benzyl group, and most preferably a halobenzyl group such as 4-chlorobenzyl. $R^6$ and $R^7$ are hydrogen, methyl, or ethyl, and represent carbon attached ring substituents. Attachment at any of the ring carbon atoms is intended. n is the integer 1, 2, or 3. Z is the oxo ($=O$), or imino ($=NH$) group.

The compounds of Formulas I and II are bases and form salts with acids. The invention includes not only the substances of Formulas I and II but also the acid addition salt thereof. The pharmaceutically acceptable acid addition salts are those in which the anion does not contribute significantly to the toxicity or pharmacological activity of the salt and, as such, they are the pharmacological equivalents of the bases of Formulas I and II. They are preferred for medical usage. In some instances they have physical properties which make them more desirable for pharmaceutical formulation purposes such as solubility, lack of hygroscopicity, compresibility with respect to tablet formation and compatibility with other ingredients with which the substances may be used for pharmaceutical purposes. The salts are made by reaction of a base of Formula I or Formula II with the acid preferably by contact in solution. They may also be made by metathesis or treatment with an ion exchange resin under conditions in which the anion of one salt of the substance of the Formula I or Formula II is replaced by the anion of another under conditions which allow for separation of the undesired species such as by precipitation from solution or extraction into a solvent, or elution from or retention on an ion exchange resin. Pharmaceutically acceptable acids for the purposes of salt formation of the substances of Formula I and II include hydrochloric, hydrobromic, hydroiodic, citric, acetic, benzoic, phosphoric, nitric, mucic, isethionic, glucosaccharic, palmitic, heptanoic, and others.

The substances of Formula I and Formula II wherein $R^1$ is hydrogen are amphoteric and also form salts with bases. Accordingly, the pharmaceutically acceptable metal, ammonium and amine salts of the substances of Formulas I and II wherein $R^1$ is hydrogen are included within the present invention. Again, the definition of pharmaceutically acceptable salt is substantially in accord with the foregoing with respect to pharmaceutically acceptable acid addition salts, but in this instance it is the cation which makes no significant contribution to toxicity or pharmacological activity. The cationic portion of these salts generally contributes to the utility of these active ingredients as the result of the physical properties of the salt for pharmaceutical reasons. The salts may be prepared as in the case of the acid addition salts by reaction of the substance of Formula I or Formula II wherein $R^1$ is H with the base preferably in solution in a reaction inert liquid medium or they can be prepared by metathesis or treatment with an ion exchange resin under conditions wherein the cation of one salt of substance of Formula I or II is replaced by another cation and the undesired species is eliminated, for instance by precipitation from solution or extraction into a solvent, or elution from or retention on an ion exchange resin. Suitable metal salts include the sodium, potassium, calcium, barium, magnesium, aluminum, and zinc salts. Similarly, the ammonium and amine salts are also considered part of the invention, these salts being prepared in substantially the same way as the metal salts from appropriate starting materials. Ammonia, ammonium hydroxide, ammonium salts, various amines, amine salts or quaternary ammonium salts and hydroxides may be employed as reactants. Suitable types of amines include:
 (a) primary, secondary or tertiary alkyl and alkenyl amines having from 1 to 22 carbon atoms and up to 3 carbon-carbon double bonds;
 (b) hydroxy substituted primary, secondary, and tertiary alkyl amines having from 1 to 22 carbon atoms and up to 3 hydroxyl groups;
 (c) the alkylenediamines having from 1 to 6 carbon atoms; and
 (d) the heterocyclic amines having from 3 to 10 carbon atoms and from 1 to 3 heteroatoms of which at least one is nitrogen.

Preferred amine salts are those of the alkyl amines having up to 6 carbon atoms or hydroxy substituted alkyl amines having up to 6 carbon atoms and 3 hydroxyl groups and the alkylenediamines having 2 to 4 carbon atoms. Suitable amines include ethylenediamine, triethylamine, tris(2-hydroxyethyl)amine, 2-hydroxyethylamine, piperidine, etc.

Compounds of Formula I and Formula II are useful as bronchodilators, antiallergy agents in the inhibition of the immediate hypersensitivity reaction, as vasodilators, and as inhibitors of the enzyme phosphodiesterase. The invention includes processes for the treatment of mammals requiring bronchodilation, vasodilation, or having allergy with a non-toxic bronchodilator effective, vasodilator effective, or immediate hypersensitivity reaction inhibiting dose of one of these compounds. The compounds may be administered orally, parenterally, topically by inhalation, or rectally. Effective doses range from about 0.03 mg./kg. of body weight up to the maximum non-toxic dose which can be administered without undue side effects. Maximum non-toxic doses can be determined by standard pharmacologic techniques using mice. The value for the substance of Procedure 3 or 4, a preferred compound for anti-asthma use, is about 250 mg./kg. of body weight per os in mice.

Compounds of Formulas I and II and their salts are believed to inhibit the degranulation of sensitized mast cells. Immediate hypersensitivity reactions such as asthma, hay fever, allergic rhinitis, urticaria, and food allergy are believed to be mediated by reaction of immunoglobulin E, sometimes referred to as reaginic antibody, with an antigen on the cell membrane of a mast cell to initiate reactions within the mast cell which ultimately release mediators such as bradykinin, histamine, serotonin or slow reacting substance-A (SRS-A). The mediators effect changes in end organs such as airways, blood vessels, skin, and mucus membranes resulting in the symptoms of an allergic attack. The present substances are believed to prevent the release of mediators thereby preventing the allergic attack. They are, therefore, useful in the prophylactic treatment of subjects possessing hypersensitivities of the foregoing types, and inhibit acute allergic attacks such as asthma, hay fever, allergic rhinitis, urticaria, and food allergy. Preferred compounds are distinguished particularly by the fact that they are orally active, have very low toxicities, and have bronchodilator action. They are thus useful in treating asthmatic attacks as well as prophylactically for hypersensitive subjects including those whose hypersensitivity is manifested by asthma. The compounds are inhibitors of rat lung phosphodiesterase, and they are peripheral vasodilators. Preferred compounds have vasodilator capacity comparable to papaverine in the dog perfused hind limb preparation.

Preferred compounds for anti-allergy and anti-asthma use are those substances of Formula I wherein $R^4$ is the substituted aralkyl group, more preferably the halobenzyl group, and most preferably wherein $R^6$, and $R^7$ are methyl or ethyl. These substances are orally effective hypersensitivity reaction inhibitors, and bronchodilators having a long duration of action. A preferred species is 4-[(4-chlorophenyl)methyl]-6,7-dihydro-6,6-dimethyl-3H-imidazo[1,2-a]-purin-9(4H)-one which is more potent than aminophylline in anti-allergy and bronchodilator action. This substance may be used for bronchodilator purposes in much the same manner as aminophylline. Oral or parenteral doses in the range of 0.03 to 250 mg./kg. of this substance may be employed. In man the estimated effective single dose is in the range of from 10–500 mg. orally and may be given from 2 to 6 times a day. Similar dosage regimens are also applicable for use thereof as an antihypersensitivity agent in asthma or allergic rhinitis.

DETAILED DESCRIPTION OF THE INVENTION

The key intermediates in the preparation of the compounds of Formula I and Formula II are the substances shown by Formula III in which B is hydrogen or the ON—, H₂N—, or

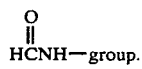
HCNH—group.

The compounds of Formula III and the acid addition salts thereof are considered part of the present invention. Some of them exhibit blocking or stimulating action on smooth muscle, e.g. 7-amino-8-[(4-chlorophenyl)-methyl]-6-formylamino-2,3-dihydroimidazo-[1,2-a]pyrimidin-5(8H)-one, and 7-amino-2,3-dihydro-6-nitroso-8-(2-phenoxyethyl)imidazo[1,2-a]-pyrimidin-5-(8H-one. Those in which B is hydrogen or the ON— group are prepared from R⁶, R⁷, substituted 2-methylmercaptoimidazolines, 2-methylmercapto-3,4,5,6-tetrahydropyrimidines, or 2-methylmercapto-3,4,5,6-tetrahydro-1,3-diazepines which are represented by Formula IV by reaction thereof with an amine of the formula R⁸NH₂, and thence in the presence of base with ethyl cyanoacetate, or ethyl oximinocyanoacetate. In

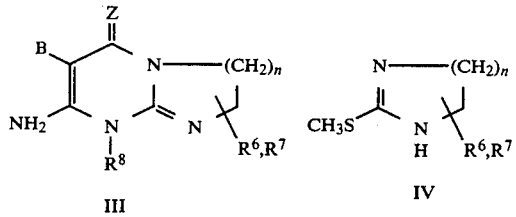

The intermediates of Formula IV are prepared by the reaction of carbon disulfide with the appropriately substituted ethylenediamine, trimethylenediamine or tetramethylenediamine followed by etherification of the resulting 2-mercaptoimidazoline, 2-mercapto-3,4,5,6-tetrahydropyrimidine or 2-mercapto-4,5,6,7-tetrahydor-1H-1,3-diazepine all according to known processes.

The following discussion of the process for the synthesis of the substances of Formula I and Formula II is directed principally to those substantes wherein n is 1, and R⁶ and R⁷ are hydrogen. Nevertheless, the method is equally applicable to all members of the series. The process is shown schematically below. R⁸ has the same meanings as described above with respect to Formula III. R⁹ is hydrogen, lower alkyl having 1 to 8 carbon atoms, or trifluoromethyl.

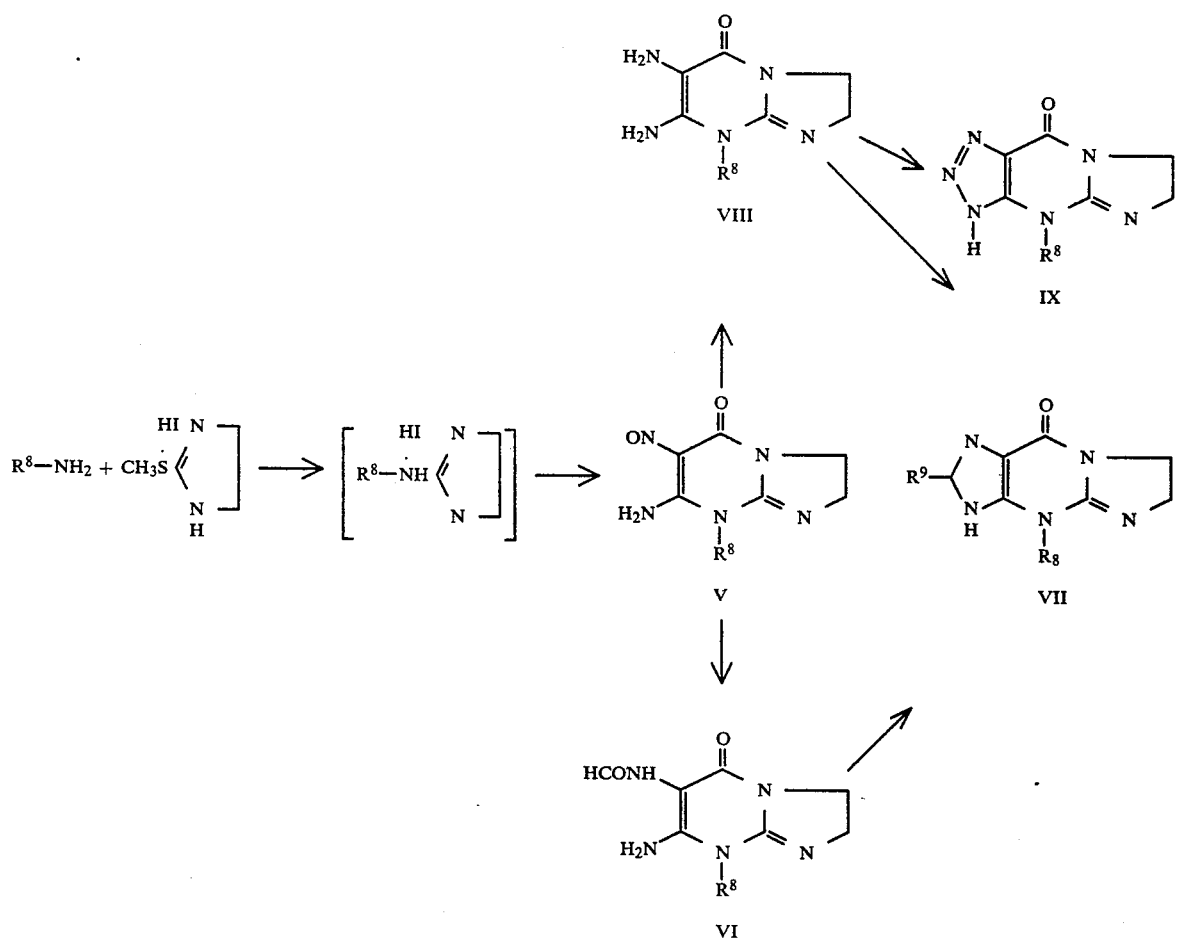

Formulas III and IV, n, Z, R⁶ and R⁷ have the same meanings as given above. R⁸ in Formula III has the same meaning as R¹ in Formula I.

Ammonia or a primary amine, is caused to react with 2-methylmercaptoimidazoline to yield a 2-aminoimidazoline in which the amino substitutent has the formula $R^8NH—$. The latter, preferably without isolation, is then caused to react in a condensation reaction with ethyl oximinocyanoacetate to give a 7-amino-2,3-dihydro-8-$R^8$-6-nitrosoimidazo[1,2a]-pyrimidin-5(8H)-one, shown by Formula V in the reaction scheme, which is the intermediate of Formula III wherein B is ON—, Z is oxo, n is 1, and $R^6$ and $R^7$ are hydrogen. The condensation reaction is carried out under anhydrous conditions in an anhydrous reaction inert liquid reaction medium in the presence of a strong base which is capable of forming the anion of the aminoimidazoline intermediate. When using a lower alkanol such as ethanol, isopropanol, or butanol as solvent, sodium ethoxide or potassium tert.-butoxide is a satisfactory base. Other alkali metal alkoxides, amides, or hydrides may be employed such as sodium amide with liquid ammonia or an aprotic liquid medium, and sodium hydride in an aprotic liquid medium. The reaction produces the intermediates of Formula V in high yields of from about 75% to 100% when $R^8$ is aralkyl or substituted aralkyl. An alternative procedure and one which is preferred when $R^8$ is an alkyl or alkenyl group is to employ ethyl cyanoacetate as reactant rather than ethyl oximinocyanoacetate. The resulting 7-amino-2,3-dihydro-8-$R^8$-imidazo[1,2-a]pyrimidin-5(8H)-one (Formula III, B, $R^6$, $R^7$=H, n=1, Z=oxo) is then nitrosated with sodium nitrite in aqueous acetic acid to yield the intermediates of Formula V.

For the preparation of the substances of Formula I, the second step in the process involves reductive formylation of the nitroso group of the substance of Formula V to yield the monoformylated diamino substance of Formula VI, which is the intermediate of Formula III wherein B is HCONH—, Z is oxo, n is 1, and $R^6$ and $R^7$ are hydrogen. The reductive formylation is carried out in formic acid as reaction medium using either catalytic reduction employing a palladium supported on carbon catalyst or sodium dithionite as reducing agent. This operation involves dissolving the nitroso compound of Formula V preferably in 97% formic acid which may require from 10 ml. to 30 ml. of 97% formic acid per gram of substance of Formula V. Other equivalent formylating reaction media may be employed. When employing catalytic hydrogenation, hydrogen pressures of from atmospheric pressure up to about 100 p.s.i. are satisfactory employing sufficient palladium supported on carbon catalyst to bring the hydrogenation to completion. A previously calibrated apparatus is convenient so that the extent of hydrogen absorption on a molecular basis can be measured. If the calculated quantity of hydrogen is not consumed before hydrogen absorption ceases, a fresh portion of catalyst is added and the hydrogenation is continued. The hydrogenation is carried out at room temperature although the process is exothermic resulting in a slight to moderate elevation in temperature depending on the batch size during the initial stages of hydrogenation. Temperatures to 20° C. to 40° C. are satisfactory. Hydrogenation usually requires a fairly short period of time of from 15 minutes to 1 hour depending upon the size of the batch and the particular apparatus employed.

When using sodium dithionite ($Na_2S_2O_4$) as reducing agent in the reductive formylation, it is simply added to a solution of the intermediate of Formula V in concentrated aqueous (87–97% by weight) formic acid. Somewhat more than a stoichiometric quantity is employed, but large excesses are not necessary since the reduction takes place more quickly than does the decomposition of the sodium dithionite. For reduction of an aromatic nitroso compound to the corresponding aromatic amino compound, two molecular proportions of sodium dithionite is a stoichiometric quantity. This is a novel and surprising process in view of the fact that the prior art has employed this reducing agent in basic solution only. Sodium dithionite is known to be decomposed in acidic media. Some sulphur is produced as a by-product during the reaction. The process is generally applicable to the reduction of aromatic nitroso compounds of the formula ArNO to aromatic amines of the formula $ArNH_2$ wherein Ar is an aromatic carbocyclic or an aromatic heterocyclic group.

Cyclization of the formyl diaminoimidazopyrimidinone of Formula VI to the 4-$R^8$-6,7-dihydro-2-$R^9$-3H-imidazo[1,2-a]purin-9(4H)one of Formula VII is achieved either by heat alone, by warming in dilute aqueous sodium hydroxide, or under the agency of a dehydrating agent such as polyphosphoric acid or an anhydride. The latter may also serve as a reagent for introducing the 2-$R^9$ substituent into the substances of Formula VII by means of an acyl interchange with the formyl group during the cyclization process. When employing an anhydride of the formula $(R^9CO)_2O$ in which $R^9$ is lower alkyl of 1 to 8 carbon atoms or trifluoromethyl as cyclization or dehydrating agent in the presence of pyridine as reaction medium, the $R^9$ substituent corresponding to the anhydride is introduced. For instance, isobutyric anhydride yields a 2-isopropyl substituted product, and trifluoroacetic anhydride yields the 2-trifluoromethyl product. The reaction is preferably carried out at the reflux temperature of the reaction mixture or within the range of about 130° C. to 170° C. employing convenient solvent amounts of anhydride and pyridine relative to the amount of Formula VI intermediate being converted, but at least one molecular proportion of anhydride. Also, the nitroso compound of Formula V may be reduced to the diamino compound of Formula VIII as described below and the latter heated at 130°–170° with a carboxylic anhydride to yield a compound of Formula VII.

For pyrolytic cyclization of the formylamino compound of Formula VI to the product of Formula VII wherein $R^9$ is hydrogen, a temperature of about 260° C. is employed after diluting the intermediate of Formula VI with sufficient dimethylformamide to afford a fluid, non-viscous liquid on heating. The diluent is removed by evaporation during the process and results in the formation of the desired product as a residual cake which is usually brown in color. Alternatively, for the cyclization to yield substances of Formula VII, $R^9$=H, triethylorthoformate may be used in combination with an alkanoyl anhydride dehydrating agent. The ethyl orthoformate suppresses the acyl interchange reaction which occurs when the anhydride is employed with pyridine. Nevertheless, the product is sometimes contaminated with low percentages of the 2-$R^9$ substituted product from the anhydride $(R^9CO)_2O$. A convenient solvent amount of a liquid anhydride is employed in combination with approximately 2 to 5 molecular proportions of ethyl orthoformate per molecular proportion of formylamino derivative. Again, the process is carried out at the reflux temperature or about within the range of 130° C. to 170° C.

For the preparation of the substances of Formula I in which $R^4$ is alkanoyl, aroyl, or substituted aroyl one convenient method is to employ the intermediate of Formula VI wherein $R^8$ is a hydrogen atom and to employ the desired alkanoyl, aroyl, or substituted aroyl anhydride as dehydrating or cyclizing agent in the transformation of the intermediate of Formula VI to the product of Formula VII as is described above. When pyridine is used as vehicle an $R^9$ substituent corresponding to the anhydride employed is also introduced. Similar conditions to those described above are employed. For instance, when 7-amino-6-formylamino-2,3-dihydroimidazo-[1,2-a]-pyrimidin-5(8H)-one is refluxed with equal volumes of pyridine and isobutyric anhydride 6,7-dihydro-2-(1-methylethyl)-4-(2-methylpropionyl)-3H-imidazo-[1,2-a]-purin-9(4H)-one is produced.

A substance of Formulas I or II wherein $R^4$ is H may be acylated in conventional fashion for the preparation of alkanoamides, arylcarboxamides, or ring-substituted arylcarboxamides using the corresponding carboxylic acid halide, anhydride, or mixed anhydride. Preferred conditions are those comparable to those known to be efficient for acylation of a weakly basic aniline derivative. In any given example, a determination should be made as to whether the $N^4$(Formula I or II wherein $R^4$ is alkanoyl, aroyl, or substituted aroyl) or $N^5$-acyl product is produced ($R^{15}$ in Formulas XV, XVI, XVIII, or XXII).

The products of Formula I and Formula II wherein $R^1$ is other than hydrogen are readily prepared by reaction of an alkali metal salt of a substance of Formula I or Formula II wherein $R^1$ is a hydrogen atom with a reagent of the formula AX wherein A has the same meaning given above, and X is a reactive ester group such as chloride, bromide, iodide, phosphate, or sulfate. The required alkali metal salt is obtained by dissolving the substance of Formula I or Formula II, $R^1$=H, in dilute aqueous sodium hydroxide or potassium hydroxide or reaction thereof with a strong alkali metal base in a reaction inert organic solvent such as an aromatic or aliphatic hydrocarbon, ether, alcohol, or amide such as dimethylformamide. Suitable bases include sodium hydride, sodium methoxide, potassium tert.-butoxide, sodium amide, or lithium hydride. Suitable reactive esters for reaction in aqueous solution or in an inert organic solvent include butyl bromide, methyl iodide, dimethylsulfate, triethyl phosphate, hexyl bromide, tert.-butyl chloride, benzyl bromide, 2-phenoxyethyl chloride, 4-fluorobenzyl bromide, 3-chlorobenzyl bromide, and 2-methoxybenzyl chloride. An elevated temperature in the range of about 80° to 150° C. is desirable.

The compounds of Formula I wherein $R^2$ is hydrogen are subject to halogenation under conventional conditions for introduction of a chlorine, bromine, or iodine atom to yield the substances of Formula I wherein $R^2$ is chlorine, bromine, or iodine. For instance, treatment of an acetic acid solution of a product of Formula I wherein $R^2$ is hydrogen with elemental bromine results in introduction of a bromine atom into the 2-position. N-Bromosuccinimide, N-chlorosuccinimide or N-chloroacetamide may also be employed for halogenation. Other suitable halogenating agents and conditions include phosphorus oxychloride or phosphorus tribromide for conversion of a 2-hydroxy group to the corresponding 2-chloro or 2-bromo compound. The 2-chloro compounds may be converted to 2-iodo or 2-fluoro compounds by reaction with concentrated (47%) aqueous HI at 0° C. or conversion to the trimethylammonium salt followed by reaction of that product with $KHF_2$ at 50° C. in the absence of any diluent.

The 4-substituted 6,7-dihydro-3H-imidazo-[2'1':5,6]-v-triazolo-[4,5-d]-pyrimidin-9(4H)-ones of Formula II are produced from the intermediates of Formula V by reduction of the nitroso group to an amino group as shown in the compound of Formula VIII in the above reaction scheme which is the intermediate of Formula III wherein B is $H_2N$—, Z is oxo, n is 1, and $R^6$ and $R^7$ are hydrogen. The reduction may be carried out in a fashion similar to the reductive formylation in the production of the intermediates of Formula VI except that formic acid is replaced by some other reaction medium which is inert under the reaction conditions. For catalytic reduction an acidic medium is preferred and an aqueous mineral acid is quite satisfactory as reaction medium. Dilute aqueous hydrochloric acid is preferred. Other methods known to those skilled in the art for reduction of a nitroso group to an amino group are also applicable. The resulting diamino intermediate of Formula VIII is then converted to the product of Formula IX by treatment under conditions usually employed for the diazotization of aromatic amines, for instance sodium nitrite and aqueous hydrochloric acid. Isolation and purification of the intermediates of Formula VIII is not necessary. The solution resulting from reduction after separation of the catalyst may be treated with an aqueous solution of sodium nitrite and then simply evaporated to afford the desired product which is then purified by recrystallization.

To summarize, there is provided according to the present invention intermediates of Formula III and a process for the conversion thereof to compounds of Formula I and Formula II which comprises first, forming the aminopyrimidine compound of Formula III wherein B is hydrogen or the ON—group, by condensation of a lower alkyl ester of cyanoacetic acid or oximinocyanoacetic acid, respectively, with a 2-$R^8$NH-1,3-diazacycloalk-2-ene and thereafter introducing the nitroso group by reaction of the product with nitrous acid when cyanoacetic ester is used as reactant, and then reducing the nitroso compound of Formula III (B is ON—) under formylating conditions when a compound of Formula I is desired and under non-formylating conditions when a compound of Formula II is desired, respectively yielding the monoformyl-diaminopyrimidine of Formula III wherein B is the HCONH— group or the diaminopyrimidine of Formula III wherein B is the $H_2N$— group and thereafter cyclizing said compound of Formula III (B is $H_2N$— or NCONH—) to yield a compound of Formula I or a compound of Formula II wherein said cyclization in the preparation of Formula I compounds is carried out by heating said substance of Formula III (B=HCONH—) at a temperature of about 260° C. in the presence of sufficient of a reaction inert diluent to afford a liquid reaction mixture or alternatively heating said substance in the presence of a cyclodehydrating agent such as polyphosphoric acid or carbocyclic acid anhydride at a temperature within the range of about 130° C. to 170° C. and wherein said cyclization in the preparation of Formula II compounds is carried out by diazotizing said substance of Formula III (B is $NH_2$) by treating with a diazotizing reagent under conditions which are known to be operable for the diazotization of aromatic amines, and thereafter when a compound of Formula I or Formula II is desired having $R^4$ alkanoyl, aroyl, or substituted aroyl reacting a substance of Formula I or II wherein $R^4$ is hydrogen with an acylating agent capable of introducing said alkanoyl, aroyl, or substituted aroyl group under conditions known for the production of amides from aromatic amines. Compounds of Formula I wherein $R^2$ is a hydrogen atom may be treated with a halogenating agent known to be suitable for introduction of a chlorine or bromine atom into an aromatic compound to produce a substance of Formula I wherein $R^2$ is chlorine or bromine and converting said chloro, or bromo compound to the corresponding fluoro, or iodo compound. Further, substances of Formulas I or II wherein $R^1$ is hydrogen may be converted to an alkali metal salt by treatment with an alkali metal hydroxide in water, or a strong alkali metal base in a reaction inert liquid reaction medium and the resulting alkali metal salt reacted with a reactive ester of the formula AX such as a halide, phosphate or sulfate to yield a substance of Formulas I or II wherein $R^1$ is the group A as defined.

DESCRIPTION OF SPECIFIC EMBODIMENTS

In the following procedures temperatures are expressed in degrees Centigrade. Melting points are corrected values according to the USP method where indicated (corr.). The nuclear magnetic resonsance (NMR) spectral characteristics refer to chemical shifts (δ) expressed as parts per million (ppm) versus tetramethylsilane as reference standard. The relative area reported for the various shifts corresponds to the number of hydrogen atoms in the individual substituent and the nature of the shift as to multiplicity is reported as broad singlet (bs), singlet (s), multiplet (m), doublet (d), triplet (t), or quadruplet (q) with coupling constant reported where appropriate. The format is NMR (solvent): δ(relative area, multiplicity, J value, and, in some instances, indicated structural characteristics). Abbreviations employed are EtOH (ethanol), HOAc (acetic acid), Ar (aromatic group), $Et_2O$ (ethyl ether), DMF (dimethylformamide), MeOH (methanol), iPrOH (isopropanol), $Me_2CO$ (acetone), $iPr_2O$ (diisopropyl ether), THF (tetrahydrofuran), $(OEt)_3CH$ (ethyl orthoformate), Nujol (mineral oil), $DMSO-d_6$ (deuterodimethylsulfoxide), IR (infrared), KBr (potassium bromide), EtOAc (ethyl acetate), d (decomposition). Others are common and have well established meanings. The infrared spectra described include only absorption wavelengths ($cm^{-1}$) having functional group identification value. Structural characteristics are noted in some instances. Unless indicated otherwise, KBr was employed as diluent for IR spectral determinations.

Procedure 1.

7-AMINO-2,3-DIHYDRO-8-[(4-CHLOROPHENYL)METHYL]-6-NITROSOIMIDAZO[1,2-a]PYRIMIDIN-5(8H)-ONE.

To a solution of 62.30 g. 0.44 mol) of 4-chlorobenzylamine in 500 ml absolute EtOH (dried over 4A molecular sieve aluminosilicate desiccant) is added 107.40 g (0.44 mol) 2-(methylthio)-2-imidazoline hydroiodide. The mixture is heated to boiling on a steam bath in an open flask and about 150 ml of the ethanol is allowed to slowly boil off over 2 hr. This solution is added while still hot to 1.76 mole of sodium ethoxide in 1650 ml absolute EtOH. To the resulting stirred, basic solution of 2-[(4-chlorophenyl)methyl]amino-2-imidazoline is then added 61.85 g (0.44 mol) crystalline (mp 129°–131°) ethyl oximinocyanoacetate in portions. The bright yellow solution is refluxed for 3 hr and then cooled to room temperature. The yellow precipitate is collected, washed with i-PrOH, and partially air-dried. The damp sodium salt is dissolved in 2000 ml $H_2O$ and acidified with glacial HOAc. The bright pink precipitate is filtered and aid-dried overnight, then oven-dried in vacuo at 100° to yield 103.05 g (77%) of pink powder, mp 238°–241° d. Recrystallization of this material from DMF-EtOH gives red crystals, mp 241° d.

Anal. Found: C, 50.68; H, 3.93; N, 22.59. NMR ($DMSO-d_6$): 3.90 [4, m, $(CH_2)_2$], 5.15 (2, s, $CH_2AR$), 7.32 (4, s, Ar). IR (Nujol): 1600–1700 $cm^{-1}$ (C=O, C=N), 3550 $cm^{-1}$ (NH).

Procedure 2.

7-AMINO-8-[(4-CHLOROPHENYL)METHYL]-6-(FORMYLAMINO)-2,3-DIHYDROIMIDAZO[1,2-a]PYRIMIDIN-5(8H)-ONE.

A 40.50 (0.133 mol) ample of unrecrystalized nitroso compound of Procedure 1 is dissolved in 950 ml. 97% HCOOH and 25.0 g. 5% Pd/C-50% $H_2O$ is added under an atmosphere of $CO_2$. The mixture is reduced on a Parr hydrogenation apparatus with a starting pressure of 50 psig. About 90% of the calculated $H_2$ consumption occurs in <15 min. with a temperature rise of 12°. The remainder is taken up during 3 hr. and the temperature returns to that of the room. The catalyst is filtered and the resulting colorless solution concentrated in vacuo to a thick syrup. The syrup dissolves in 500 ml. $H_2O$ and is neutralized with concentrated $NH_4OH$ with cooling. The off-white solid is filtered and air-dried to yield 41.90 g. (98%), mp 272°–275° d. Recrystallization from MeOH-i-PrOH gives white crystals, mp 275.0° d. (corr.).

Anal. Found: C, 52.74; H, 4.46; N, 22.01. NMR ($DMSO-d_6$): 8.38–7.72 (2, multiple signals for N$\underline{H}$CHO conformers), 4.00 [4, m, $(CH_2)_2$], 5.90 (2, s, $C\underline{H}_2AR$), 7.25 (4, s, Ar). IR (Nujol): 3420 $cm^{-1}$ (NH), 3340, 3200 $cm^{-1}$ ($NH_2$), 1680, 1620, 1580 $cm^{-1}$ (formamide, lactam, C=N).

Procedure 3.

4-[(4-CHLOROPHENYL)METHYL]-6,7-DIHYDRO-3H-IMIDAZO[1,2-a]PURIN-9(4H)-ONE.

A suspension of 45.88 g. (0.14 mol) of formylamino derivative of Procedure 2 in a mixture of 130 ml. acetic anhydride (1.4 mol) and 65 ml. $(OEt)_3CH$ (0.39 mol) is refluxed for 5 hr. (a solution forms after 30 min.). Concentration in vacuo to about ¼ of the original volume produces an oil which dissolves in 300 ml. $H_2O$. The mixture is treated with charcoal and filtered, and the clear filtrate neutralized with conc $NH_4OH$. The white precipitate is filtered and oven-dried in vacuo to yield 28.06 g. (66%) off-white solid, mp 285°–290° C. Recrystallization from DMF-i-PrOH gave off-white crystals, mp 289°–293° C. (corr. mp 284.0°–285.0°). If this material is shown by NMR to contain solvated DMF, it may be removed by stirring the suspended solid in $ET_2O$, and then redrying.

Anal. Found: C, 55.96; H, 4.40; N, 23.16. NMR ($DMSO-d_6$, ppm): 3.84 [4, m, $(CH_2)_2$], 5.10 (2, s, $CH_2AR$), 7.50 (4, s, Ar), 7.91 (1, s, $\underline{CH}$). IR (Nujol): 1620 $cm^{-1}$ (C=N), 1680 $cm^{-1}$ (C=O).

The hydrochloride salt of the product of Procedure 3 was prepared by dissolving 21.7 g. of this material in 75 ml. of 3N HCl. Dissolution was not complete when a white solid commenced to precipitate. Water, 100 ml., was added and the mixture was heated to dissolve the precipitate. The solution was treated with decolorizing carbon and filtered. Isopropanol, 150 ml., was added to the warm filtrate and the product precipitated on cooling. It was collected, dried in a vacuum oven at 80° overnight, yield 17.05 g., mp 249.0°–250.0° d. (corr.).

Anal. Found: C, 49.75; H, 3.83; N, 20.92.

Procedure 4.
PYROLYTIC METHOD FOR THE PRODUCT OF PROCEDURE 3.

A slurry of 7.20 g. (0.022 mol) of the product of Procedure 2 in a small volume of DMF was inserted in an oil bath at 260°. The DMF evaporated rapidly, and the residual cake was heated 12 min. with constant agitation. The residual light-brown solid, mp 280°–285°, weighed 6.36 g. (93%). Recrystallization from DMF gave material identical to that obtained by Procedure 3.

Various amines were subsituted for 4-chlorobenzylamine in the method of Procedure 1 and the resulting nitrosoimidazopyrimidinones were converted according to Procedure 2 to the corresponding formylaminoimidazopyrimidinones which were then converted according to either Procedure 3 or Procedure 4 to one of the products of the present invention. Characterizing data and preparative information relative to these products are listed in Table I.

9(4H)-ONE. The method of Procedure 14 was repeated with the substitution of acetic anhydride for propionic anhydride. The resulting product was obtained as a cream-colored solid, mp 311.5°–313.5° (corr.), recrystallized from DMF-i-PrOH.

Anal. Found: C, 56.72; H, 4.36; N, 22.35. NMR (DMSO-$d_6$): 2.36 (3,s), 3.91 (4,m), 5.20 (2,s), 7.90 (4,m). IR 755, 804, 1020, 1294, 1510, 1630, 1690, 3050, 3160.

Procedure 16.
4-[(2-CHLOROPHENYL)METHYL]-2-(1-METHYLETHYL)-6,7-DIHYDROIMIDAZO[1,2-a]PURIN-9(4H)-ONE. 2-Chlorobenzylamine is substituted for 4-chlorobenzylamine in the process of Procedure 1 and the resulting nitrosoimidazopyrimidinone is converted to the corresponding formylamino compound according to the method of Procedure 2, and the resulting product is then reacted with isobutyric anhydride in a mixture of isobutyric anhydride and pyridine according to the method of Procedure 14 to give the

TABLE I

Procedures 5–13
6,7-Dihydroimidazo [1,2-a]purin-9-(4H)—ones
of Formula I, n = 1, $R^1$, $R^2$, $R^6$, $R^7$ = H

| No. | $R^4$ | m.p. °C. (corr.) | Method | Yield | Recryst. Solvent | Elemental Analysis | | NMR | IR |
|---|---|---|---|---|---|---|---|---|---|
| 5 | 3-chlorobenzyl | 262.0–267.0 | Proc. 3 | 27% | DMF | C,<br>H,<br>N, | 56.05<br>4.14<br>23.20 | (DMSO-$d_6$): 3.89 (4,m)<br>5.15 (2,s), 7.48 (4,m),<br>7.98 (1,s), 13.5<br>(1, bs) | 760, 800, 1400<br>1550, 1625, 1700,<br>2600, 2880, 2975,<br>3110 |
| 6 | 2-chlorobenzyl | 292.0–293.0 | Proc. 3 | 54% | DMF | C,<br>H,<br>N, | 55.60<br>4.01<br>23.21 | (DMSO-$d_6$): 3.84 (4,m)<br>5.20(2,s), 7.42(4,m),<br>8.01(1,s), 13.4(1,bs) | 756, 1295, 1360<br>1550, 1620, 1700,<br>2880, 2960, 3100 |
| 7 | 3,4-dichlorobenzyl | 279.0–280.0 | Proc. 3 | 96% | MeOH | C,<br>H,<br>N, | 50.09<br>3.29<br>20.53 | (DMSO-$d_6$): 3.86(4,m),<br>5.10(2,s), 7.54(3,m),<br>7.89(1,s), 13.4(s,bs) | 770, 1140, 1305<br>1440, 1480, 1560,<br>1635, 1700, 2900,<br>3140 |
| 8 | 4-fluorobenzyl HCl salt | 296.0–298.0<br>251.0–252.0 | Proc. 4 | 71% | DMF—<br>MeOH—i-<br>PrOH | C,<br>H,<br>N, | 58.98<br>4.30<br>24.41 | (DMSO-$d_6$): 3.85(4,m),<br>5.14(2,s), 7.49(4,m),<br>8.01(1,s), 13.5(1,bs) | 835, 1220, 1450,<br>1550, 1625, 1690,<br>3130 |
| 9 | 2-methoxybenzyl | 228.5–233.5 | Proc. 4 | 34% | 1N HCl—<br>NH$_4$OH | C,<br>H,<br>N, | 58.62<br>5.18<br>23.23 | (DMSO-$d_6$) 3.79(3,s),<br>4.15(4,m), 5.39(2,s),<br>7.20(4,m), 8.22(1,s) | 755, 1240, 1292,<br>1490, 1550, 1610,<br>1700, 2600, 3130 |
| 10 | 2-pyridylmethyl | 258.0–260.0 | Proc. 4 | 50% | DMF | C,<br>H,<br>N, | 56.28<br>4.38<br>29.95 | (DMSO-$d_6$): 3.80(4,m)<br>5.18(2,s), 7.24(2,m)<br>7.76(1,m), 7.85(1,2),<br>8.70(1,m) | 796, 1360, 1472,<br>1560, 1610, 1705<br>2980, 3130, 3520 |
| 11 | 2-(3,4-dimethoxyphenyl)ethyl | 218.0–224.0 | Proc. 4 | 52% | 1N HCl—<br>NH$_4$OH | C,<br>H,<br>N, | 54.80<br>5.68<br>18.55 | (DMSO-$d_6$): 2.90(2,m),<br>3.78(6,s), 3.90(9,m)<br>4.70(2,m), 6.90(3,m)<br>7.98(1,s) | 760, 1265, 1520,<br>1630, 1690, 2970, |
| 12 | 2-(phenoxy)ethyl | 223.5–224.5 | Proc. 3 | 58% | MeOH | C,<br>H,<br>N, | 60.56<br>5.09<br>23.48 | (DMSO-$d_6$): 3.90(4,m),<br>4.37(4,m), 7.26(5,m)<br>8.04(1,s) | 690, 752, 1240,<br>1500, 1625, 1705,<br>2960, 3060, 3120 |
| 13 | isobutyl | 230.5–231.5 | Proc. 4 | 34% | i-PrOH | C,<br>H,<br>N, | 56.53<br>6.54<br>29.84 | (DMSO-$d_6$): 0.92(6,d<br>6.5 Hz), 2.32(1,m),<br>3.82(6,m), 7.90(1,s) | 765, 895, 1300,<br>1436, 1550, 1620<br>1700, 2970 |

Procedure 14
4-[(4-CHLOROPHENYL)METHYL]-2-ETHYL-6,7-DIHYDROIMIDAZO[1,2-a]PURIN-9(4H)-ONE.
A mixture of 25.00 g. (0.078 mol) of the product of Procedure 2 and 50 ml. dry pyridine in 50 ml. (0.388 mol) of propionic anhydride was heated at reflux for 3 hr. Upon cooling, a white solid precipitated. CH$_3$CN was added, and the white solid filtered and air-dried to give crystals, mp 278.0°–279.0° (corr.). The material may be recrystallized from DMF-i-PrOH.

Anal. Found: C, 58.28; H, 4.76; N, 21.34. NMR (DMSO-$d_6$): 1.22 (3, t, 7.5 Hz), 2.67 (2, 9, 7.5 Hz), 3.98 (4, m), 5.08 (2, s), 7.43 (4, m), 11.3 (1, bs). IR: 756, 805, 1295, 1510, 1630, 1695, 3050, 3100, 3160.

Procedure 15.
4-[(4-CHLOROPHENYL)METHYL]-6,7-DIHYDRO-2-METHYLIMIDAZO[1,2-a]PURIN-desired product. Obtained as a fluffy white crystalline solid, mp 249.5°–255.0° after recrystallization from a mixture of chloroform and acetonitrile.

Anal. Found: C, 59.34; H, 5.54; N, 20.22. NMR (DMSO-$d_6$): 2.10 (6,d, 6.5 Hz); 2.94 (2, septet, 6.5 Hz), 3.84 (4,m), 5.12 (2,s), 7.30 (4,m). IR 760, 1300, 1505, 1626, 1692, 2980, 3180.

Procedure 17.
2-BROMO-4-[(4-CHLOROPHENYL)METHYL]-6,7-DIHYDRO-3H-IMIDAZO[1,2-a]PURIN-9(4H)-ONE HYDROBROMIDE. Bromine, 1.60 g. (0.010 mol), was added to a solution of 2.00 g. (0.0066 mol) of the product of Procedure 3 in 10 ml. HOAc and the resulting solution heated on a steam bath for 10 min. Yellow flakes precipitated and were filtered and air-dried to give 3.29 g. solid, mp 212° d. Heating a suspension of the material in CH₃CN gave a white powder, mp 248° d. Recrystallization from DMF-CH₃CN gave fine, white needles, mp 228.5°–229.5° d (corr.).

Anal. Found: C, 36.48; H, 2.92; N, 15.01.

Procedure 18.

7-AMINO-8-BENZYL-2,3-DIHYDRO6-NITROSOIMIDAZO[1,2-a]PYRIMIDIN-5(8H)-ONE. The method of Procedure 1 is repeated with the substitution of benzylamine for 4-chlorobenzylamine. Product melting point 242° d., 68% yield, recrystallized from DMF.

Procedure 19.

7-AMINO-2,3-DIHYDRO-6-FORMYLAMINOIMIDAZO[1,2-a]PYRIMIDIN-5(8H)-ONE. The method of Procedure 2 is applied to the product of Procedure 18 to yield this product, m.p. 268° d., yield 40%. The product was not recrystallized.

Procedure 20.

6,7-DIHYDRO-2-(1-METHYLETHYL)-4-(2-METHYLPROPIONYL)-3H-IMIDAZO[1,2-a]PURIN-9(4H)-ONE. The method of Procedure 14 was applied to the product of Procedure 19 with the substitution of isobutyric anhydride for the propionic anhydride specified in Procedure 14. The product was obtained in 35% yield, m.p. 271.0°–273.0° (corr.) after recrystallization from isopropanol.

Anal. Found: C, 58.50; H, 6.25; N, 24.39. NMR (DMSO-d₆): 1.20 (6,d), 1.34 (6,d), 3.00 (1,m), 4.10 (5,m), 13.2 (1,bs). IR: 780, 1250, 1275, 1365, 1410, 1540, 1580, 1700, 2980, 3200.

Procedure 21.

7-AMINO-8-[(4-FLUOROPHENYL)METHYL]-6-(FORMYLAMINO)-2,3-DIHYDROIMIDAZO[2,3-a]PYRIMIDIN-5(8H)-ONE. 7-Amino-2,3-dihydro-8-[(4-fluorophenyl)methyl]-6-nitrosoimidazo[1,2-a]pyrimidin-5(8H)-one is prepared by the method of Procedure 1 with substitution of 4-fluorobenzylamine for-4-chlorobenzylamine which is used in that example. To the resulting product 9.79 g. (0.034 mol), mp 223.5°–225.5° d (corr.) in 100 ml. 97% HCOOH at room temperature is added 15.00 g. (0.086 mol) Na₂S₂O₄ in portions over about 5 min. The solution turns from dark purple to light yellow during the resulting exothermic reaction, and some yellow precipitate forms. The mixture is stirred for 10 min., then concentrated in vacuo to about 25 ml. The residual is dissolved in 150 ml. H₂O, filtered, and neutralized with concentrated NH₄OH The white precipitate is collected, slurried in hot MeOH, and filtered. Oven drying in vacuo yields 9.25 g. (90%) white solid, mp 248°–250°. Recrystallization from MeOH yields white crystals, mp 262° d.

Anal. Found: C, 55.20; H, 4.62; N, 22.87.

The formylamino compound produced by Procedure 21 was converted according to the method described in Procedure 4 to yield a product identical to that produced in Procedure 8.

Procedure 22.

7-AMINO-8-(PHENYLMETHYL)-2,3-DIHYDRO-6-(FORMYLAMINO)IMIDAZO[1,2-a]-PYRIMIDIN-5(8H)-ONE. The method of Procedure 21 is applied to the product of Procedure 18 to prepare this material in 86% yield, mp 248°–250° after recrystallization from DMF-i-PrOH.

Anal. Found: C, 58.84; H, 5.38; N, 24.31. NMR (DMSO-d₆): 3.79 (4,m), 5.30 (2,s), 6.66 (2,bs), 7.50 (5,m), 8.36 (1,s), 8.82 (1,s). IR: 700, 740, 1305, 1500, 1580, 1612, 1655, 3200, 3320, 3400.

Procedure 23.

4-(PHENYLMETHYL)-6,7-DIHYDRO-3H-IMIDAZO[1,2-a]PURIN-9(4H)-ONE. The product of Procedure 22 is substituted as formylamino starting material in the method of Procedure 3. The product is obtained in 64% yield as a light yellow crystalline solid, mp 262°–264° (corr.) after recrystallization from DMF-i-PrOH.

Anal. Found: C, 62.57; H, 5.15; N, 26.13. NMR (DMSO-d₆): 3.88 (4,m), 5.16 (2,s), 7.45 (5,m), 8.00 (1,s). IR: 715, 764, 1300, 1435, 1550, 1620, 1700, 3150.

Procedure 24.

1-BUTYL-4-[(4-CHLOROPHENYL)METHYL]-6,7-DIHYDROIMIDAZO[1,2-a]PURIN-9(4H)-ONE HYDROCHLORIDE. To a stirred suspension of 1.77 g. (0.0059 mol) the product of Procedure 3 in 20 ml. dry DMF was added 0.27 g. (0.0065 mol) NaH (57% mineral oil dispersion). When dissolution was complete, 0.69 g. (0.0065 mol) n-butyl bromide was added, and the mixture was heated at 100° for 3 hr. Water (200 ml.) was added, and the aqueous portion decanted from the precipitated gum. The gum was dissolved in 100 ml. 1 N HCl and was filtered. The resulting yellow solution was made basic with NH₄OH. and the resulting gum was taken up in i-PrOH. The i-PrOH solution was acidified with ethanolic HCl and allowed to evaporate. The solid residue was recrystallized from CH₃CN-EtOAc to give 0.65 g. (28%) pale-yellow crystals, mp 223°–225° (corr. mp 205.5°–206.5° d).

Anal. Found: C, 54.48; H, 5.56; N, 17.84. NMR (CDCl₃): 0.83 (3,t, 6.2 Hz), 1.27 (2,m), 1.73 (2, m), 4.28 (6, m), 5.88 (2, s), 7.39 (2, m), 8.04 (1, s). IR: 770, 1310, 1480, 1500, 1608, 1660, 1720, 2710, and 3110.

Procedure 25.

4-[(4-CHLOROPHENYL)METHYL]-6,7-DIHYDRO-3H-IMIDAZO[2′,1′:5,6]-v-TRIAZOLO[4,5-d]PYRIMIDIN-9(4H)-ONE. A solution of 1.00 g. (0.0033 mole) of the product of Procedure 1 in 50 ml. 1 N HCl was hydrogenated over 0.50 g. 10% Pd/C. The catalyst was filtered, and the filtrate cooled to 0°. A solution of 0.24 g. :0.0035 mole; NaNO₂ in 2 ml. H₂O was added in one portion, and the solution was stirred at 25° C. for 30 min. The solution was concentrated in vacuo to a solid residue which was slurried in MeOH and filtered. The filtrate was concentrated in vacuo, and the crystalline residue slurried in CH₃CN and filtered to yield 0.60 g. pink crystals, mp 252° d. The material was dissolved in 1 N NaOH and neutralized with HOAc. The white solid was filtered and air-dried to yield 0.50 g. (50%), mp>300.0°.

Anal. Found: C, 51.30; H, 4.02; N, 27.65. NMR (DMSO-d₆+CF₃CO₂H): 4.26 (4, m), 5.57 (2, s), 7.79 (5, m). IR: 770, 810, 1305, 1495, 1585, 1640, 1720, and 2700.

Various nitrosoimidazolopyrimidinones prepared as intermediates in the various procedures described herein may be converted according to Procedure 25 to the corresponding imidazotriazolopyrimidinones. Refer, for instance, to Procedures 5–13, 18, 31, and 41–43. Similarly, the 1-substituted imidazotriazolopyrimidinones may be prepared from the corresponding unsubstituted compounds by application of the methods illustrated in Procedures 24, and 32–44. Characterizing data and preparative information relative to some of these products are listed in Table II.

TABLE II

Procedures 26–29
6,7-Dihydro-3H—imidazo[2'1':5,6]-v-triazolo[4,5-d]-
pyrimidin-9(4H)—ones of Formula II n = 1, $R^1$, $R^6$, and $R^7$ = H

| Proc. No. | $R^4$ | mp °C. (Corr.) | Yield | Recyrst. Solvent | Elemental Analysis | | NMR | IR |
|---|---|---|---|---|---|---|---|---|
| 26 | 3,4-dimethoxyphenethyl | 286.0–287.0 | 51% | 1 N NaOH—HOAc | C,<br>H,<br>N, | 55.46<br>5.27<br>24.07 | (CF$_3$CO$_2$H): 4.03 (6,s),<br>3.32 (2,m), 4.50 (6,m)<br>7.08 (3,m) | 775, 1305, 1520,<br>1580, 1650, 1725,<br>2700 |
| 27 | 4-fluorobenzyl | 294.0–295.0 d. | 29% | 1 N NaOH—HOAc | C,<br>H,<br>N, | 54.30<br>3.86<br>29.08 | (DMSO-d$_6$): 4.00 (4,m)<br>5.21 (2,s), 7.41 (4,m) | 770, 830, 1300,<br>1510, 1580, 1640,<br>1720, 2700 |
| 28 | 3,4-dichlorobenzyl | 247.5–249.5 d. | 43% | water | | | (DMSO-d$_6$): 4.21 (4,m)<br>5.72 (2,s), 7.85 (3,m) | 825, 1320, 1590,<br>1665, 1755, 2800,<br>3000 |
| 29 | hydrogen* | >300 | 9% | 1 N NaOH—HOAc | C,<br>H,<br>N, | 40.05<br>3.62<br>46.27 | (DMSO-d$_6$): 3.90 (4,m)<br>8.20 (1,bs) | 780, 1280, 1540,<br>1620, 1700, 3080,<br>3160 |

*Prepared by substitution of o-methoxybenzylamine in the method of Procedure 1 followed by reduction and cyclization of that product by the method of Procedure 25; debenzylation occurred resulting in the formation of the $R^4$ hydrogen product indicated.

Procedure 30.

7-AMINO-2,3-DIHYDRO-8-(2-METHYL-PROPYL)IMIDAZO[1,2-a]PYRIMIDIN-5(8H)-ONE. A mixture of 29.25 g. (0.40 mole) isobutylamine and 48.82 g. (0.20 mole) 2-(methylthio)-2-imidazoline hydroiodide in 250 ml. abs. EtOH were refluxed for 2 hr. The mixture was concentrated in vacuo to a viscous-oil, which was dissolved in 100 ml. abs. EtOH and added to a solution of 8.40 g. (0.80 mole) sodium and 22.62 g. (0.20 mole) ethyl cyanoacetate in 1200 ml. abs. EtOH. The mixture was refluxed for 3 hr., then concentrated in vacuo to a viscous oil. Water (400 ml.) was added and a white solid slowly crystallized. The solid was filtered and air-dried to yield 35.43 g. (86%), mp 235°–238° (two crops). Recrystallization from CH$_3$CN gave white crystals, mp 230.5°–232.5° (corr.).

Anal. Found: C, 57.75; H, 7.93; N, 27.14. NMR (DMSO-d$_6$): 0.89 (6, d, J 6.0 Hz), 2.04 (1, m), 3.68 (2, d), 3.76 (4, m), 4.38 (1,s), 7.68 (2, bs). IR: 770, 1190, 1280, 1490, 1610, 1655, 3160, and 3300.

Procedure 31.

7-AMINO-2,3-DIHYDRO-8-(2-METHYL-PROPYL)-6-NITROSOIMIDAZO[1,2-a]PYRIMIDIN-5(8H)-ONE. To a solution of 5.00 g. (0.024 mole) of the product of Procedure 30 in 15 ml. H$_2$O and 4 ml. HOAc (0°) was added (portionwise) 1.72 g. (0.024 mole) NaNO$_2$. The mixture was stirred at 24° for 30 min., cooled to 0° and filtered to yield 4.44 g. (72%) of a purple solid, mp 203°–205° d.

Recrystallization from H$_2$O provided pink needles, mp 205°–207°.

Anal. Found: C, 45.56; H, 7.16; N, 26.93.

The product of Procedure 31 is then converted to the product of Procedure 13 by reduction to the corresponding formylamino compound by the method of Procedure 2 and cyclization by the method of Procedure 4.

Procedures 32–40.

The method of Procedure 24 is applied to the product of Procedure 13 with the substitution of the following reactants for n-butyl bromide to yield the analogous products which are listed in Table III.

TABLE III

Procedures 32–40
1-$R^1$—6,7-Dihydro-4-(2-methylpropyl)-imidazo[1,2-a]purin-9(4H)—ones of
Formula I, n = 1, $R^2$, $R^6$, and $R^7$ = H, $R^4$ = 2-methylpropyl

| Proc. No. | Reactant | $R^1$ |
|---|---|---|
| 32 | 4-fluorobenzyl chloride | F—⟨phenyl⟩—CH$_2$— |
| 33 | 3,4-dichlorobenzyl chloride | Cl—⟨phenyl⟩—CH$_2$—<br>Cl |
| 34 | 2-methoxybenzyl chloride | ⟨phenyl⟩—CH$_2$—<br>OCH$_3$ |
| 35 | 2-(4-chlorophenyl)ethyl bromide | Cl—⟨phenyl⟩—CH$_2$CH$_2$— |
| 36 | 3-chloromethylpyridine | ⟨pyridine⟩—CH$_2$— |
| 37 | 4-chloromethylpyridine | N⟨pyridine⟩—CH$_2$— |
| 38 | 3-bromo-2-methylpropene | CH$_2$=C(CH$_3$)—CH$_2$— |
| 39 | 2-phenoxyethyl bromide | ⟨phenyl⟩—OCH$_2$CH$_2$—* |
| 40 | 2-naphthylmethyl bromide | ⟨naphthyl⟩—CH$_2$— |

*Yield 53%, hydrochloride salt recrystallized from CH$_3$CN, mp 228–230°.
Anal. Found: C, 58.75; H, 6.18; N, 17.88
NMR (CDCl$_3$): 1.10 (6,d, 6.2 Hz), 2.40(1,m), 4.41 (8,m), 4.83 (2,t, 6.0 Hz), 7.21 (5,m), 8.06 (1,s), 13.7 (1,bs).
IR: 700, 760, 1250, 1460, 1600, 1645, 1715, 2600, 2980.

Procedure 41.

4-[(4-CHLOROPHENYL)METHYL]-6,7-DIHYDRO-6,7-DIMETHYL-3H-IMIDAZO[1,2-a]PURIN-9(4H)-ONE. Procedure 1 is repeated with substitution of 4,5-dimethyl-2-(methylthio)-2-imidazoline hydroiodide for the 2-(methylthio)-2-imidazoline hydroiodide specified. The resulting 7-amino-2,3-dihydro-2,3-dimethyl-8-[(4-chlorphenyl)methyl]-6-nitrosoimidazo[1,2-a]pyrimidin-5(8H)-one is converted to the corresponding 6-formylamino compound by the method of Procedure 2 and the latter is converted to the desired product by the method of Procedure 4.

Procedure 42

4-[(4-CHLOROPHENYL)METHYL]-7,8-DIHYDRO-3H,6H-PYRIMIDO[1,2-a]PURIN-10(4H)-ONE. Procedure 1 is repeated with substitution of 2-(methylthio)-3,4,5,6-tetrahydropyrimidine hydroiodide for the 2-(methylthio)-2-imidazoline hydroiodide specified. The resulting 8-amino-3,4-dihydro-9-[(4-chlorophenyl)methyl]-7-nitroso-2H,5H-pyrimido(1,2-a) pyrimidin-6(9H)-one is converted to the corresponding 7-formylamino compound according to the method of Procedure 2, and the latter is then cyclized to the desired product by the method of Procedure 4.

Procedure 43.

4-[(4-CHLOROPHENYL)METHYL]-6,7,8-TETRAHYDRO-3H-1,3-DIAZEPINO[1,2-a]PURIN-11(4H-ONE. Procedure 1 is repeated with substitution of 2-(methylthio)-4,5,6,7-tetrahydro-1H1,3-diazepine hydroiodide for the 2-(methylthio)-2-imidazoline hydroiodide specified. The resulting 9-amino-10-[(4-chlorophenyl)methyl]-8-nitroso-2,3,4,5-tetrahydro-1,3-diazepino[1,2-a]-pyrimidin-7(1OH)-one is converted to the corresponding 8-formylamino compound by the method of Procedure 2, and the latter is then cyclized to the desired product by the method of Procedure 4.

Procedure 44.

1,4-Di[4-FLUOROPHENYL)METHYL]-6,7-DIHYDROIMIDAZO[1,2-a]PURIN-9(4H)-ONE.
The method of Procedure 24 is applied to the product of Procedure 8 with substitution of 4-fluorobenzyl chloride for the n-butyl bromide specified in Procedure 24. The product is recovered in 53% yield, recrystallized from isopropyl acetate-hexane, mp 186.0°–188.0° (corr.).

Anal. Found: C, 63.76; H, 4.54; N, 17.50. NMR (CDCl3): 4.03 (4, m), 5.25 (2, s), 5.45 (2, s), 7.34 (8, m), and 7.57 (1, s). IR: 760, 775, 834, 1230, 1520, 1648, and 1690.

Procedure 45.

4-[(4-CHLOROPHENYL)METHYL]-2-TRIFLUOROMETHYL-6,7-DIHYDROIMIDAZO[1,2-a]PURIN-9(4H)-ONE. A solution of 25.0 g. (0.078 mol) of the product of Procedure 2 in 100 ml. of trifluoroacetic anhydride is prepared and chilled in an ice bath. Several drops of pyridine are then carefully added. The mixture is then treated as described in Procedure 14 for separation and recovery of the desired product.

Procedure 46.

2-BROMO-4-[(4-CHLOROPHENYL)METHYL]-6,7-DIHYDRO-1-METHYL-1H-IMIDAZO[1,2-a]PURIN-9(4H)ONE. The product of Procedure 17 is allowed to react with iodomethane under alkaline conditions according to the method of Procedure 67 to give the desired product, m.p. 206°–207°.

Anal. Found: C, 45.77; H, 3.28; N, 17.68. NMR (DMSOd6): 3.77 (3, s); 3.81 (4, m); 4.98 (2, s); 7.36 (4, s). IR: 750, 1335, 1525, 1580, 1630, 1680, and 2940.

Procedure 47.

4-[(4-CHLOROPHENYL)METHYL]-6,7-DIHYDRO-1-METHYL-2-[(2-METHYLPROPYL)AMINO]-1H-IMIDAZO-[1,2-a]PURIN-9(4H)-ONE.
A mixture of the product of Procedure 46, 1.0 g. (0.0025 mole) and 0.37 g. (0.005 mole) of 2-methylpropylamine in 20 ml. of ethanol is refluxed for 16 hrs. The desired product precipitated as the hydrobromide salt which was collected and mixed with dilute aqueous sodium hydroxide to convert it into the free base form, m.p. 185°–187°.

Anal. Found: C, 58.48; H, 5.97; N, 21.45. NMR (DMSOd6): 0.88 (6, d, 6.2 Hz); 2.05 (1, m); 3.09 (2, t, 6.5 Hz); 3.27 (2, bs); 3.50 (3, s); 3.75 (4, m); 4.93 (2, s); 6.78 (1, bs); 7.36 (4, m). IR: 740, 1460, 1490, 1560, 1615, 1680, 2950, and 3330.

Procedure 48.

2-AZIDO-4-[(4-CHLOROPHENYL)METHYL]-6,7-DIHYDRO-1-METHYLIMIDAZO[1,2-a]PURIN-9(4H)-ONE. The method of Procedure 47 is repeated with the substitution of sodium azide for 2-methylpropylamine. In this instance 100 ml. of abs. ethanol is used as solvent. The product is recovered by removal of insoluble material from the reaction mixture by filtration and evaporation of the filtrate.

Procedure 49.

4-[(4-CHLOROPHENYL)METHYL]-2-CYANO-1-METHYL-6,7-DIHYDROIMIDAZO[1,2-a]PURIN-9(4H)-ONE. The method of Procedure 48 is repeated with substitution of NaCN for sodium azide.

Procedure 50.

2-DIBUTYLAMINO-4-[(4-CHLOROPHENYL)METHYL-1-METHYL-6,7-DIHYDROIMIDAZO[1,2-a]PURIN-9(4H)-ONE. The method of Procedure 47 is repeated with the substitution of dibutylamine for 2-methylpropylamine.

When lower boiling amines such as ethyl amine, or ammonia are substituted in Procedure 47 to yield a 2-loweralkylamino- or a 2-amino compound, the process is carried out in a closed vessel under pressure to afford the necessary reaction temperature. Higher boiling precursor amines such as benzylmethylamine may be employed with subsequent hydrogenolysis of the benzyl group to yield, for instance, the 2-methylamino compound.

Procedure 51.

SOLUTION FOR INJECTION.

The following ingredients are dissolved in sufficient water for injection to make 1 liter and the solution is filtered through a membrane filter having a pour size of 0.5 micrometers.

| Ingredient | Amount |
| --- | --- |
| Product of Procedure 27 | 0.2–5.0 g. |
| Sodium Chloride, q.s. isotonic | |
| tris(hydroxymethyl)aminomethane | |
| buffer, q.s., pH 8.5 | |

The filtered solution is filled into clean sterile ampules and flame sealed followed by sterilization in an autoclave.

Procedure 52.

TABLETS FOR ORAL INGESTION.

The following ingredients are blended in the dry state in a twin-shell blender and compressed on a tablet press using an 11/32 inch die and concave punches.

| Ingredient | Amount |
| --- | --- |
| Product of Procedure 3 | 50.0 g. |
| Sucrose, pregranulated for direct compression | 210.0 g. |
| Corn starch | 6.0 g. |
| Microcrystalline cellulose | 40.0 g. |
| Magnesium stearate | 1.0 g. |

This batch size is for 1,000 tablets and provides a tablet weighing 370 mg. supplying 50 mg. of active ingredient per tablet. Tablets containing from 25 to 200 mg. of active ingredient may be made employing the same ingredients but adjusting the weight and tablet size appropriately.

Procedure 53.

POWDER FOR INHALATION.

The following ingredients are blended aseptically and filled into hard gelatin capsules, each containing 50 mg. of the mixture providing 25 mg. of the active ingredient.

| Ingredient | Amount |
| --- | --- |
| Product of Procedure 4, micronized | 25.0 g. |
| Lactose powder | 25.0 g. |

The foregoing is sufficient for 1,000 capsules. These capsules are suitable for dispensing the powder into the inspired air stream using a breath actuated device. Appropriate adjustments of the composition can be made to given capsules containing 0.5 to 40 mg. of active ingredient.

FURTHER DETAILED DESCRIPTION OF THE INVENTION

A number of additional compounds of a sort similar to those defined by Formula I and Formula II above have useful bronchodilator activity, antiallergy activity of the mediator release inhibiting type, vasodilator activity, and phosphodiesterase enzyme inhibitory activity. Furthermore, certain additional compounds, for instance, those of Procedures 12 and 58, 6,7-dihydro-4-(2-phenoxyethyl)-3H-imidazo[1,2-a]purin-9(4H)-one and 6,7-dihydro-2-methyl-4-(2-phenoxyethyl-)imidazo[1,2-a]purin-9(4H)-one, respectively, have been found to have anticholinergic action of a type which mediates improved bronchodilator activity. Formulas XX and XI below correspond to Formulas I and II and redefine the scope of the invention to include all of these additional substances which are illustrated in Procedures 46, 47, 54–84, 97, 98, 100–102, 104, 106–114, 116, 117, 120–122 and 124–131. Further, other additional substances sharing one or more of the foregoing biological properties are isomeric with those of Formulas XI and XX and are defined by Formulas XII, XV, and XVI, and XXII illustrated in Procedures 85–95, 119 and 126. They are also considered part of the present invention as are pharmaceutically acceptable acid addition and quaternary ammonium salts (illustrated in Procedures 94 and 123) of the compounds of Formulas I, II, XI, XII, XIV, XV, XVI, XVII, XVIII, XX, XXII, and XXIII, and the pharmaceutically acceptable metal, ammonium, and amine salts of those members wherein $R^{11}$ is hydrogen.

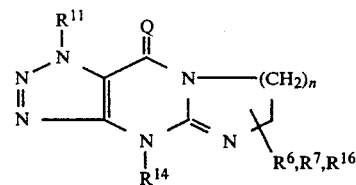

Formula XI

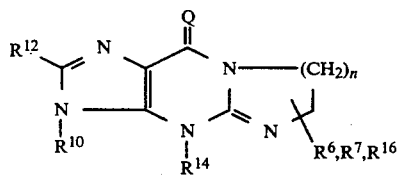

Formula XII

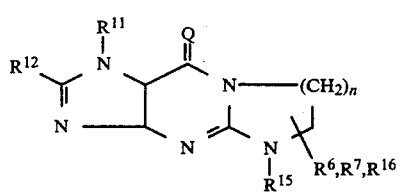

Formula XV

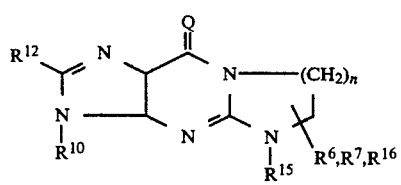

Formula XVI

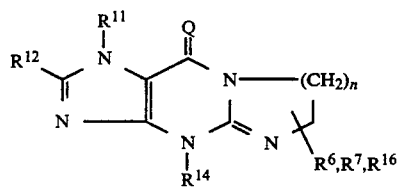

Formula XX

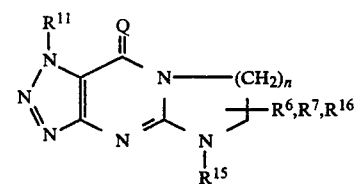

Formula XXII

In the foregoing formulas,

Q is O, S, or $NR^{10}$, $R^{10}$ is selected from the group consisting of hydrogen, lower alkyl having up to 8 carbon atoms, lower alkenyl or lower alkynyl each having 3 to 8 carbon atoms, dialkylaminoalkyl having 4 to 12 carbon atoms cycloalkyl having 3 to 6 carbon atoms, cycloalkylalkyl having 4 to 12 carbon atoms, pyridylmethyl, aralkyl or substituted aralkyl each having 7 to 12 carbon atoms, aryloxyalkyl or substituted aryloxyalkyl each having 8 to 12 carbon atoms wherein each of said substituted aralkyl, and substituted aryloxyalkyl groups contains 1 or 2 substituents selected from halogen, alkoxy, and alkyl, and each of said alkoxy and alkyl groups contains up to 6 carbon atoms, $R^{11}$ is alkoxycarbonyl having 2 to 4 carbon atoms, aminoalkyl having 2 to 8 carbon atons, or is independently selected from the foregoing group defined for $R^{10}$, $R^{12}$ is lower alkyl, lower alkenyl, lower alkynyl, lower alkylthio, lower alkylsulfinyl, or lower alkylsulfonyl each having up to 8 carbon atoms, hydrogen, thiono, trifluoromethyl or halogen when $R^{11}$ is hydrogen, $R^{12}$ is lower alkylamino, di-lower alkylamino, lower alkoxyimino, lower alkyl, lower alkenyl, lower alkynyl, lower alkylthio, lower alkylsulfinyl, lower alkylsulfonyl, or lower alkoxy each having up to 8 carbon atoms, hydrogen, thiono, trifluoromethyl, halogen, hydrazino, azido, cyano, hydroxy, or amino when $R^{11}$ is other than hydrogen, $R^{14}$ and $R^{15}$ are selected from the group consisting of hydrogen, lower alkyl having up to 8 carbon atoms, lower alkenyl or lower alkynyl having 3 to 8 carbon atoms, cycloalkyl having 3 to 6 carbon atoms, cycloalkylalkyl having 4 to 12 carbon atoms, pyridylmethyl, lower alkanoyl or lower alkenoyl or lower alkynoyl each having up to 8 carbon atoms, aroyl or substituted aroyl having 7 to 12 carbon atoms, aralkyl or substituted aralkyl having 7 to 12 carbon atoms, aryloxyalkyl or substituted aryloxyalkyl having 8 to 12 carbon atoms wherein each of said substituted aroyl, substituted aralkyl, and substituted aryloxyalkyl groups contains 1 or 2 ring substituents selected from halogen, alkoxy, and alkyl, and each of said alkoxy and alkyl groups contains up to 6 carbon atoms, $R^6$ and $R^7$ represent hydrogen or a carbon attached ring substituent selected from methyl and ethyl, $R^{16}$ represents a double bond between adjacent ring carbon atoms or up to 2 hydrogen atoms as necessary to form a saturated structure, and no more than two of $R^6$, $R^7$, and $R^{16}$ are located on the same ring carbon atom, n is the integer 1, 2, or 3.

When $R^{10}$, $R^{11}$, $R^{14}$, or $R^{15}$ contains a disubstituted aralkyl group, a disubstituted aryloxyalkyl group, or a disubstituted aroyl group having adjcent substituents according to the foregoing definitions, those combinations of adjacent substituents which are sterically incompatible, that is substituents incapable of occupying adjacent positions such as adjacent tertiary alkyl groups, are not intended by the formulas.

The compounds for Formula XX and Formula XI are prepared by the same methods described above with respect to the compounds of Formula I and Formula II. For the preparation of the compounds of Formula XX and Formula XI which are not included within Formula I and Formula II, the methods previously described can be adapted to the preparation of these new compounds by the appropriate selection of starting materials to afford the desired substituent groups, $R^{11}$, $R^{12}$, and $R^{14}$. The compounds of Formulas XX and XII, and Formulas XV and XVI wherein $R^{11}$ is H are tautomers and do not enjoy a separate existence in the pure crystalline state.

The compounds of Formula XII wherein $R^{10}$ is other than hydrogen are prepared from the intermediates of Formula XIII by the same methods previously described with respect to preparation of the compounds of Formula I from those of Formula III. This is illustrated in Procedures 85–89. In Formula XIII, $R^{18}$ is defined by the same terms as $R^{10}$. $R^{18}$ and $R^{10}$ may be the same or different.

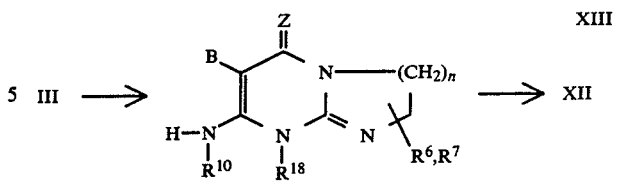

The conversion of an intermediate of Formula III and analogs thereof where $R^8$ is replaced by $R^{18}$ into an intermediate of Formula XIII can be carried out by any of the known methods for the preparation of a secondary amine from a primary aromatic amine. One method is by reductive alkylation wherein an aldehyde or ketone is caused to condense with the 7-amino group of the intermediate of Formula III wherein B is hydrogen under reductive conditions so that the Schiff's base which is first formed is reduced under the reaction conditions to yield the $R^{10}$ substituent. An aldehyde or ketone of the appropriate structure to yield the desired $R^{10}$ structure on reduction of the intermediate Schiff's base is selected. This is specifically illustrated in Procedures 85 and 86.

The substances of Formula XII wherein $R^{10}$ is other than hydrogen and Q is $NR^{10}$ may sometimes be prepared by a method similar to that described above for the preparation of the substances of Formula I wherein $R^1$ is other than hydrogen involving reaction of an alkali metal salt of a substance of Formula XX wherein $R^{11}$ is hydrogen and Q is $NR^{10}$ with a reagent of the formula DX wherein D has the same meaning given above for A and also includes alkynyl having 3 to 8 carbon atoms, cycloalkyl having 3 to 6 carbon atoms, and cycloalkylalkyl having 4 to 12 carbon atoms and X has the same meaning given above. The reaction is carried out in the same manner as described above. In some instances, the pure substance of Formula XII wherein Q is $NR^{10}$ is obtained while in others it may be obtained in a mixture with the substance of Formula XX wherein $R^{11}$ is other than hydrogen and Q is $NR^{10}$.

The reaction scheme shown above with respect to Formulas V, VI, VII, VIII, IX, and X may be readily adapted to the preparation of the compounds of Formulas XV and XXII wherein $R^{15}$ is other than hydrogen by substitution of an intermediate of Formula XIX for the intermediate of Formula X in that scheme.

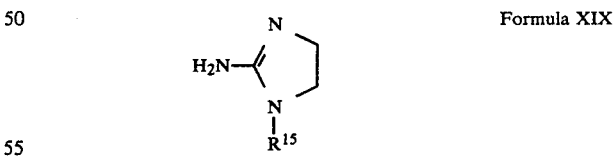

Formula XIX

Such intermediates are readily prepared from an alkylenediamine of the formula $R^{15}NH(CH_2)_nNH_2$ wherein n=2, carbon disulfide, and methyl iodide followed by reaction of the resulting 1-$R^{15}$-2-methylthioimidazolinium iodide with ammonia. $R^{15}$ and n have the same meaning as previously given. This is illustrated in Procedures 90–93, and 126 hereof.

Another method for the preparation of the compounds of Formula XV which is particularly adapted to the preparation of those substances wherein $R^{15}$ is lower alkyl having up to 8 carbon atoms involves forming the quaternary ammonium salt of a substance of Formula XX wherein $R^{14}$ is the benzyl or substituted benzyl group with a lower alkyl halide, phosphate, sulfate, or other reactive ester group which results in the formation of a lower alkyl-substituted quaternary ammonium nitrogen atom at the 5-position. The latter is then hydrogenated by chemical or catalytic means resulting in hydrogenolysis of the $R^{14}$ benzyl or substituted benzyl group and elimination of a proton to yield the tertiary amine pictured in Formula XV. This is illustrated in Procedures 94 and 95.

The substances XVI wherein $R^{10}$ is other than hydrogen are made in a fashion analogous to those of Formula XII wherein $R^{10}$ is other than hydrogen and illustrated in Procedures 85–89 via the intermediates of the Formula XXI or by the alternative alkylation method similar to that described with respect to Formula XII from Formula XV wherein $Q=NR^{10}$ and $R^{10}=H$. The intermediates of Formula XXI are also part of the present invention.

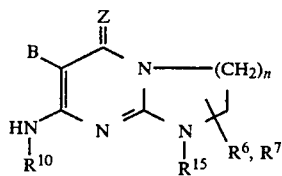

Formula XXI

The substances of Formulas XI, XII, XV, XVI, XX, and XXII, wherein Q is sulphur are prepared by reaction of a compound of Formula XI, XII, XV, XVI, XX, or XXII, wherein Q is oxygen under conditions known for the transformation of a carboxamide or a ketone into a thiocarboxamide or a thione. One suitable method is by heating the oxo compound with phosphorus pentasulfide preferably in the presence of pyridine as reaction medium. This is specifically illustrated in Procedure 75.

Those compounds of Formulas XI, XII, XV, XVI, XX, and XXII wherein Q is $NR^{10}$ are prepared from the compounds of Formulas XIV, XVII, XVIII, or XXIII which are shown below. These compounds and their pharmaceutically acceptable acid addition and quaternary ammonium salts also have bronchodilator or antiallergy activity are are considered part of the present invention.

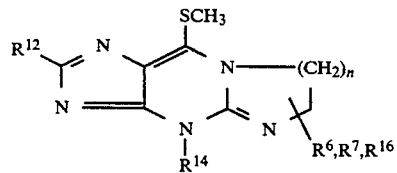

Formula XIV

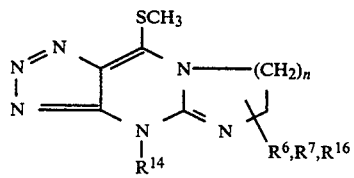

Formula XVII

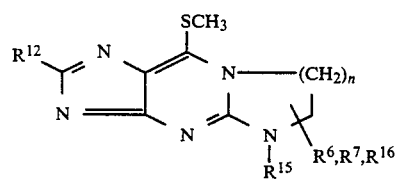

Formula XVIII

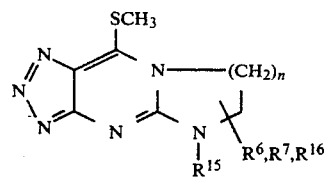

Formula XXIII

The compounds of Formula XIV, XVII, XVIII, and XXIII are prepared from those of Formula XI, XV, XX, and XXII wherein $R^{11}$ is hydrogen and Q is sulphur by reaction with methyl iodide in the presence of a base such as sodium hydroxide. For instance, the reaction may be carried out in aqueous solution by dissolving the substance of Formula XX wherein $Q=S$ in aqueous sodium hydroxide containing slightly more than one molecular proportion of the latter and adding methyl iodide thereto. The desired intermediate of Formula XIV precipitates forthwith from the aqueous mixture. This is illustrated in Procedure 76. It is then converted to a compound of Formulas XX wherein $R^{11}$ is hydrogen and Z is $=NR^{10}$ by reaction of the substance of Formula XIV with an amine of the Formula $R^{10}NH_2$. This is illustrated in Procedure 77.

The pharmaceutically acceptable quaternary ammonium salts of the substances of Formulas I, II, XI, XII, XIV, XV, XVI, XVII, XVIII, XX, XXII, and XXIII, are also considered part of the present since these salts share the biological properties of the substances defined by these formulas, and, in some instances, possess other desirable properties in addition such as, for instance, anticholinergic activity. The term pharmaceutically acceptable primarily has reference to the anion which does not contribute significantly to the toxicity or pharmacological activity of these salts as is the case with the pharmaceutically acceptable acid addition salts described above. They are prepared by reaction preferably of an equimolar proportion of a reactive ester of the formula $R^{17}X$ wherein $R^{17}$ is a group other than hydrogen as defined for $R^{10}$ and X is chloride, bromide, iodide, phosphate, or sulfate as defined above. Preferably $R^{17}$ is lower alkyl having up to about 8 carbon atoms. A reaction inert liquid reaction medium is ordinarily employed.

Those substances of the present invention wherein $R^{16}$ is a double bond between adjacent carbon atoms of the ring are prepared by $MnO_2$ oxidation of the corresponding saturated compound. This is illustrated in Procedure 124. It is preferred to apply this method of those substances which have no other readily oxidizable $R^{10}$, $R^{11}$, $R^{12}$, $R^{14}$, or $R^{15}$ substituent. Even when such substituent is present, however, it is usually possible to isolate the desired product in low yield.

FURTHER DESCRIPTION OF SPECIFIC EMBODIMENTS

The products of Procedures 54–63 were prepared by substituting the amine corresponding to the $R^{14}$ substituent in the method of Procedure 1 and converting the resulting nitrosoimidazopyrimidinone to the corresponding formylaminoimidazopyrimidinone according to Procedure 2. The latter were then cyclized to the desired products of Formula XX either by refluxing with acetic anhydride and ethyl orthoformate according to Procedure 3, pyrrolyzing in an oil bath at 260° C. employing a small amount of DMF as vehicle in some instances according to Procedure 4, or by refluxing with pyridine and the appropriate carboxylic acid anhydride to provide the desired $R^{12}$ substituent according to Procedure 14. These preparations are summarized in Table IV.

TABLE IV

Procedures 54-63
Formula XX
$Q = O, n = 1, R^6, R^7, R^{11},$ and $R^{16} = H$

| Proc. No. | $R^{12}$ | $R^{14}$ | m.p. °C. (Corr.) | Method | Recryst. Solvent | Elemental Analysis | | NMR | IR |
|---|---|---|---|---|---|---|---|---|---|
| 54 | H | n-octyl | 150.0–155.0 | Proc. 3 | EtOAc | C, H, N, | 62.42 7.86 24.08 | (CDCl$_3$): 0.89 (3,m), 1.28 (12,m), 4.14 (6,m), 7.76 (1,s) | 765, 1300, 1355, 1470, 1560, 1640, 1695, 2865, 2940, 3110 |
| 55 | methyl | n-octyl | 201.5–203.5 | Proc. 14 | DMF/CH$_3$CN | C, H, N, | 63.15 8.48 23.11 | (DMSO-d$_6$): 0.85 (3,t, 6.5 Hz), 1.27 (10,m) 1.69 (2,m), 2.31 (3,s), 3.82 (6,m) | 755, 1295, 1340, 1515, 1620, 1630, 1700, 2855, 2930, 3150 |
| 56 | isopropyl (hydrochloride salt dihydrate) | n-octyl | 235.0–245.0 | Proc. 14 | i-PrOH | C, H, N, | 53.56 8.51 17.48 | (DMSO-d$_6$): 0.88 (3,t, 6.8 Hz), 1.23 (12,m), 1.38 (6,d, 7.0 Hz), 4.18 (6,m) | 756, 1300, 1605, 1630, 1725, 2860, 2930, 3440 |
| 57 | H | Cl—⟨C$_6$H$_4$⟩—OCH$_2$CH$_2$— | 251.5–253.5 | Proc. 4 | DMF | C, H, N, | 54.14 4.56 20.95 | (DMSO-d$_6$): 3.82(4,m), 4.31 (4,s), 7.18 (4,m), 7.94 (1,s) | 760, 1050, 1240, 1300, 1500, 1630, 1700, 2600, 2880, 2970 |
| 58 | methyl | ⟨C$_6$H$_5$⟩—OCH$_2$CH$_2$— | 215.0–221.0 | Proc. 14 | MeOH | C, H, N, | 61.46 5.53 22.69 | (DMSO-d$_6$): 2.32 (3,s) 3.86 (4,m), 4.30 (4,m), 7.12 (5,m) 13.20(1,bs) | 700, 763, 1055, 1255, 1510, 1525, 1630, 1705, 2850, 2900 |
| 59 | H | cyclohexyl-methyl | 245.0–251.0 | Proc. 3 | i-PrOH/CH$_3$CN | C, H, N, | 61.55 7.15 25.37 | (DMSO-d$_6$): 1.13 (4,m), 1.13 (7,m) 3.88 (6,m), 7.92 (1,s) | 760, 1300, 1465, 1550, 1620, 1700, 2860, 2930 |
| 60 | H | Cl—⟨C$_6$H$_4$⟩—CH$_2$CH$_2$— | 259.0–216.0 | Proc. 4 | DMF/CH$_3$CN | C, H, N, | 57.05 4.48 22.20 | (DMSO-d$_6$): 3.04 (2,t, 7.0 Hz), 3.90 (4,m), 4.16 (2,t, 7.0 Hz), 7.42 (4,m), 7.96 (1,s), 12.50 (1,bs) | 760, 1360, 1490, 1550, 1610, 1695, 2600, 2880, 2960 |
| 61 | isopropyl | isobutyl | 248.5–249.5 | Proc. 14 | MeOH/CH$_3$CN | C, H, N, | 61.19 7.60 25.60 | (CDCl$_3$): 0.99 (6,d, 6.5 Hz), 1.45 (6,d, 7.0 Hz), 2.50 (1,m) 3.21 (1,septet, 7.0 Hz), 3.96 (2,d, 7.0 Hz), 4.10 (4,m) | 758, 1295, 1510, 1550, 1620, 1635, 1700, 2880, 2970, 3170 |
| 62 | H | C$_6$H$_5$CH$_2$CH$_2$CH$_2$— | 227.0–229.0 | Proc. 14 | DMF/CH$_3$CN | C, H, N, | 64.78 5.63 23.68 | (DMSO-d$_6$): 2.03 (2,m), 2.68 (2,t, 7.0 Hz), 3.92 (6,m), 7.44 (5,s), 8.12 (1,s) | 700, 742, 760, 1290, 1550, 1610, 1640, 1695, 2600, 2950 |
| 63* | methyl | isobutyl | 234.0–236.0 | Proc. 14 | CH$_3$CN | C, H, N, | 58.30 6.74 28.44 | (CDCl$_3$): 0.96 (6,d, 6.5 Hz), 2.49 (1,m), 2.52 (3,s), 3.88 (2,d, 7.2 Hz), 4.11 (4,m) | 755, 1210, 1295, 1440, 1520, 1620, 1695, 2830, 3150 |

*The method used was as follows:
A solution of 15.2 g. (0.05 mole) of the nitroso compound of Procedure 31 in methanol was hydrogenated over 10% Pd/C catalyst until the calculated quantity of hydrogen had been absorbed. The catalyst was filtered, and the solvent removed from the filtrate by concentration in vacuo. The residual 6,7-diamino-8-(2-methylpropyl)imidazo[1,2-a]pyrimidin-5-(8H)—one was immediately treated with acetic anhydride, 50 ml., and the solution was heated at reflux for 45 to 60 min. The acetic anhydride was then removed by distillation in vacuo leaving a brown solid residue which was triturated with acetonitrile and collected by filtration, yield 6.56 g., m.p. 227–232°. Recrystallization from acetonitrile gave the product identified in the table.

Procedures 64–65.
VARIOUS 6,7-DIHYDRO-2-$R^{12}$-4-$R^{14}$-3H-IMIDAZO[1,2-a]PURINE-9(4H)-ONES. 7-Amino-2,3-dihydro-6-formylaminoimidazo[1,2-a]pyrimidine-5(8H)-one (Procedure 19) is treated with various carboxylic acid anhydrides according to the method of Procedure 14 resulting in the production of various substances of Formula XX wherein $R^{12}$ and $R^{14}$ have the meanings given in Table V.

TABLE V

Procedures 64–65
Formula XX
$Q = O, n = 1, R^6, R^7, R^{11},$ and $R^{16} = H$

| Procedure No. | Carboxylic Acid Anhydride | $R^{12}$ | $R^{14}$ |
|---|---|---|---|
| 64 | propiolic | HC≡C— | HC≡CC(=O)— |
| 65 | acrylic | H$_2$C=CH— | H$_2$C=CHC(=O)— |

Procedure 66.

6,7-DIHYDRO-1-(2-METHYLPROPYL)-4-OCTYLIMIDAZO[1,2-a]PURIN-9(4H)-ONE HYDROCHLORIDE. 6,7-Dihydro-4-octyl-3H-imidazo[1,2-a]purin-9(4H)-one (Procedure 54) was converted to the sodium salt, and the sodium salt was treated with isobutyl bromide all as described in Procedure 24. The crude product in the base form was recovered as an oil which was identified as reaction product by thin layer chromatography (silica, CHCl$_3$—EtOH, 80:20) and purified by chromatography on silica using CHCl$_3$—CH$_3$CN (graded elution). The product was then dissolved in ethyl acetate and treated with ethanolic HCl to yield the hydrochloride salt as a white crystalline solid, m.p. 113.0°–116.5°. It was shown by analysis to be the desired product containing 0.25 mole water of hydration.

Anal. Found: C, 59.05; H, 8.48; N, 18.12. NMR (CDCl$_3$): 0.90 (3,m), 0.97 (6,d, 6.6 Hz), 1.35 (12,m), 2.00 (1,m), 4.33 (8,m), 7.81 (1,s). IR: 760, 1320, 1470, 1605, 1640, 1720, 2860, 2940, and 3480.

Procedure 67.

4-[(4-CHLOROPHENYL)METHYL]-6,7-DIHYDRO-1-METHYL-1H-IMIDAZO[1,2-a]PURIN-9(4H)-ONE. 4-[(4-Chlorophenyl)methyl]-6,7-dihydro-3H-imidazo-[1,2-a]purin-9(4H)-one (Procedure 3), 6.02 g. (0.02 mole), is dissolved with warming in a mixture of 100 ml. of water and 15 ml. of ethanol containing 1.0 g. (0.25 mole) of sodium hydroxide. Approximately 3 ml. (approximately a molar equivalent) of methyl iodide was added and the mixture was stirred for about 48 hrs. at room temperature. The precipitated solid was collected, air dried, and recrystallized from isopropanol, m.p. 182.5°–184.5°.

Anal. Found: C, 56.98; H, 4.39; N, 22.19. NMR (CDCl$_3$): 3.90 (3,s), 3.98 (4,m), 5.14 (2,s), 7.35 (5,m). IR: 760, 1350, 1495, 1550, 1580, 1640, 1690, 2880, and 3120.

Procedures 68–69.

1-R$^{11}$-4-[(4-CHLOROPHENYL)METHYL]-6,7-DIHYDROIMIDAZO[1,2-a]PURIN-9(4H)-ONES. The substances identified in Table VI were prepared by substitution of the reactants listed in the table for n-butyl bromide in the process of Procedure 24. The products may be recovered from the reaction mixture by the application of the techniques described herein.

TABLE VI

Procedures 68–69
Formula XX
Q = 0, n = 1, R$^6$, R$^7$, R$^{12}$, and R$^{16}$ = H
R$^{14}$ = Chlorophenylmethyl

| Proc. No. | Reactant | R$^{11}$ |
|---|---|---|
| 68 | bromocyclohexane | cyclohexyl |
| 69 | cyclopropylmethyl chloride | cyclopropylmethyl |

Procedures 70–73.

6,7-DIHYDROIMIDAZO-4-R$^{14}$-IMIDAZO[1,2-a]PURIN-9(4H)-ONES. The amines listed below are substituted in Procedure 1 for 4-chlorobenzylamine. The resulting 7-amino-2,3-dihydro-8-R$^{14}$-6-nitrosoimidazo[1,2-a]pyrimidin-5(8H)-ones are then converted to the corresponding 7-amino-8-R$^{14}$-6-(formylamino)-2,3-dihydroimidazo[1,2-a]pyrimidin-5(8H)-ones by the method of Procedure 21. The latter are then cyclized by the method of procedures 3 or 4 to yield the desired product. The reactants employed and products obtained are listed in the following table.

TABLE VII

Procedures 70–73
Formula XX
Q = 0; n = 1; R$^6$, R$^7$, R$^{11}$, R$^{12}$, and R$^{16}$ = H

| Proc. No. | Reactant | R$^{14}$ |
|---|---|---|
| 70 | allylamine | CH$_2$=CHCH$_2$— |
| 71 | 1-amino-2-propyne | CH≡CCH$_2$— |
| 72 | cyclohexylamine | cyclohexyl |
| 73 | cyclopropylmethylamine | cyclopropylmethyl |

Procedure 74.

6,7-DIHYDRO-4-(2-PHENOXYETHYL)-3H-IMIDAZO [2',1':5,6]-v-TRIAZOLO[4,5-d]PYRIMIDIN-9(4H)-ONE. 7-Amino-2,3-dihydro-8-(2-phenoxyethyl)-6-nitrosoimidazo[1,2-a]pyrimidin-5(8H)-one was prepared by the method of Procedure 1 with substitution of 2-phenoxyethylamine on a molecular basis for the 4-chlorobenzylamine specified in that procedure. This material was then converted by hydrogenation and diazotization as described in Procedure 25 to the desired product which was purified by dissolving in IN aqueous sodium hydroxide with warming and acidification with acetic acid, m.p. 302.0°–303.0° dec.

Anal. Found: C, 56.15; H, 4.79; N, 28.00. NMR (DMSO-d$_6$): 4.02 (4,m), 4.43 (4,s), 7.15 (5,m). IR: 700, 770, 1255, 1315, 1508, 1595, 1655, 1730, and 2740.

Procedure 75.

4-[(4-CHLOROPHENYL)METHYL]-6,7-DIHYDRO-3H-IMIDAZO[1,2-a]PURIN-9(4H)-THIONE. The product of Procedure 3, 6.02 g. (0.02 mole), phosphorus pentasulfide, 12.0 g. (0.054 mole), and 125 ml. of pyridine were heated at reflux with stirring for 5 hrs. The dark solution was cooled to 45° and poured into 1 liter of water and the resulting mixture cooled by the addition of ice. The solid was collected on a funnel, dissolved in dilute aqueous sodium hydroxide, the dark colored solution treated with decolorizing carbon, filtered and the yellow filtrate acidified (about pH 6) with acetic acid. The yellow solid was collected after cooling and air dried; recrystallized from DMF/CH$_3$CN; m.p. 254.0°–256.0° dec.

Anal. Found: C, 52.72; H, 3.95; N, 22.19. NMR (DMSO-d$_6$): 4.00 (4,m), 5.05 (2,s), 7.41 (4,m), 7.92 (1,s), 13.00 (1,bs). IR: 810, 1090, 1290, 1460, 1590, 1650, 2880, 2960, and 2960.

Procedure 76.

4-[(4-CHLOROPHENYL)METHYL]-6,7-DIHYDRO-9-(METHYLTHIO)IMIDAZO[1,2-a]PURINE. The product of Procedure 75, 6.65 g. (0.021 mole), was dissolved in a mixture of 100 ml. of water and 15 ml. of ethanol containing 1.0 g. (0.025 mole) of sodium hydroxide. Methyl iodide, 7.09 g. (0.05 mole) was then added whereupon a precipitate commenced to form and developed into a thick slurry within 3 hrs. The solid was collected, air dried, and recrystallized from DMF with charcoal treatment, m.p. 254.0°–256.0° dec.

Anal. Found: C, 54.15; H, 4.19; N, 21.32. NMR (DMSO-d$_6$ +DCl): 2.43 (3,s), 41.3 (4,m), 5.56 (2,s), 7.50 (4,m) 8.25 (1,s). IR: 1105, 1160, 1300, 1315, 1550, 1570, 1665, 2880, 2950, and 3100.

Procedure 77. 4-[(4-CHLOROPHENYL)METHYL]-6,7-DIHYDRO-9-IMINO-3H,4H-IMIDAZO[1,2-a]PURINE. The product of Procedure 76, 2.26 g. is suspended in a solution of about 6 g. of ammonia in 100 ml. of ethanol. Further anhydrous ammonia was added to yield a substantially saturated solution. The mixture was then placed in a pressure apparatus and heated at 100° overnight with agitation. The container was cooled to room temperature, opened, and the supernatent liquid decanted from the yellow solid. The precipitated solid and the residue obtained on evaporation of the supernatant liquid proved to be identical by infrared and thin-layer chromatography. They were combined and recrystallized from DMF, recovered as the hydrate containing ¼ mole water of hydration, m.p. 296°–299°.

Anal. Found: C, 55.39; H, 4.36; N, 27.70. NMR (DMSO-d$_6$): 3.95 (4,m), 5.05 (2,s), 7.32 (1,s), 7.41 (4,m). IR: 700, 740, 1300, 1410, 1490, 1560, 1600, 1670, 2880, and 3150.

Various amines of the formula $R^{10}NH_2$ may be substituted for ammonia in Procedure 77 to provide various other substances of Formula XX wherein Q is $R^{10}N$. The amine, $R^{10}NH_2$, is preferably employed in approximately equimolar amount with the reactant of XIV.

Procedures 78–84.

VARIOUS 2-$R^{12}$-4-[(4-CHLOROPHENYL)METHYL]-1-METHYL-6,7-DIHYDROIMIDAZO[1,2-a]PURIN-9(4H)-ONES. The method of Procedure 47 is adapted to the preparation of these substances by the substitution of the following starting materials on a molecular basis for the 2-methylpropylamine specified in Procedure 47. Where a volatile starting material is specified, a pressure vessel is employed to carry out the reaction.

TABLE VIII

Procedures 78–84
Formula XX
$Q = 0, n = 1, R^6, R^7, R^{16} = H, R^{11} = CH_3,$
$R^{14} = $ 4-Chlorophenylmethyl

| Procedure No. | $R^{12}$ | Starting Material |
|---|---|---|
| 78* | H$_2$NNH— | hydrazine |
| 79 | n-BuONH— | O—butylhydroxylamine |
| 80 | n-BuO— | n-butanol |
| 81 | CH$_2$=CH(CH$_2$)$_6$O— | 7-octenol |
| 82 | CH$_3$C≡CCH$_2$O— | 2-butynol |
| 83 | HO— | potassium acetate, water |
| 84* | H$_2$N— | ammonia |

*Procedure 78.

4-[(4-CHLOROPHENYL)METHYL]-2-HYDRAZINO-6,7-DIHYDRO-1-METHYL-1H-IMIDAZO[1,2-a]PURIN-9(4H)-ONE. Recrystallized from EtOH, m.p. 218.5°–220.5° d.

Anal. Found: C, 51.76; H, 4.65; N, 28.08. NMR (DMSO-d$_6$): 3.50 (3, s); 3.78 (4, m); 4.25 (2, bs); 4.99 (2, s); 7.35 (4, m); 7.90 (1, bs). IR: 745, 1460, 1490, 1550, 1600, 1625, 1680 and 3330.

*Procedure 84.

2-AMINO-4-[(4-CHLOROPHENYL)METHYL]-6,7-DIHYDRO-1-METHYL-1H-IMIDAZO[1,2-a]PURIN-9(4H)-ONE HYDRATE. Recrystallized from MeOH, m.p. 259°–261°.

Anal. Found: C, 53.83; H, 4.51; N, 24.97. NMR (DMSO-d$_6$): 3.28 (1, bs); 3.50 (3, s); 3.76 (4, m); 4.92 (2, s); 6.60 (bs, 2); 7.32 (4, s). IR: 740, 1460, 1490, 1540, 1600, 1630, 1680, and 3440.

Procedures 85–89

Formula XII $R^{10} = $ 4-Chlorophenylmethyl, $R^{14} = $ 2-Methylpropyl

Procedure 85.
7-[(4-CHLOROPHENYL)METHYLENE]AMINO-2,3-DIHYDRO-8-(2-METHYLPROPYL)IMIDAZO[1,2-a]PYRIMIDIN-5(8H)-ONE. A mixture of 7-amino-2,3-dihydro-8-(2-methylpropyl)imidazo[1,2-a]pyrimidin-5(8H)-one (Procedure 30) (0.2 mol), 4-chlorobenzyldehyde (0.2 mol) and a catalytic quantity of p-toluenesulfonic acid in 1 l. toluene is heated under reflux until the theoretical amount of water is azeotropically removed.

Procedure 86.

7-[(4-CHLOROPHENYL)METHYL]AMINO-2,3-DIHYDRO-8-(2-METHYLPROPYL)IMIDAZO[1,2-a]PYRIMIDIN-5(8H)-ONE. A mixture of the product of Procedure 85 (0.15 mol) and sodium borohydride (0.16 mol) in 250 ml. ethanol is stirred and refluxed for 4 hrs., then concentrated in vacuo. The residue is purified by recrystallization.

Procedure 87.

7-[(4-CHLOROPHENYL)METHYL]AMINO-2,3-DIHYDRO-8-(2-METHYLPROPYL)-6-NITROSOIMIDAZO[1,2-a]PYRIMIDIN-5(8H)-ONE. A suspension of the product of Procedure 86 (0.1 mol) in 150 ml. 25% aqueous acetic acid is cooled to 0° C. and treated by dropwise addition of an aqueous solution of sodium nitrite (0.11 mol). After stirring at 0° C. for an hour, the mixture is warmed to room temperature, the solid collected by filtration, washed with water and air dried.

Procedure 88.

7-[(4-CHLOROPHENYL)METHYL]AMINO-6-FORMYLAMINO-2,3-DIHYDRO-8-(2-METHYLPROPYL)IMIDAZO[1,2-a]PYRIMIDIN-5(8H)-ONE. To a stirred solution of the nitroso compound of Procedure 87 (0.1 mol) in 200 ml. formic acid, sodium dithionite (0.25 mol) is added portionwise. After one hour, the reaction mixture is concentrated in vacuo, the residue dissolved in water and filtered. The filtrate is made basic with concentrated aqueous ammonia, and the product collected.

Procedure 89.

3-[(4-CHLOROPHENYL)METHYL]-6,7-DIHYDRO-4-(2-METHYLPROPYL)-3H-IMIDAZO[1,2-a]PURIN-9(4H)-ONE. The formyl amino compound of Procedure 88 (0.08 mol) is dissolved with warming in a solution of sodium hydroxide (0.09 mol) in 100 ml. water. The solution is treated with activated charcoal, filtered, and the filtrate neutralized with acetic acid. The precipitate is collected.

Procedures 90–93

Formula XV $R^{15} = $ 4-Chlorophenylmethyl

Procedure 90.

N-[(4-CHLOROPHENYL)METHYL]ETHYLENEDIAMINE. p-Chlorobenzyl chloride, 32 g. (0.2 mole), was added dropwise to 60 g. (1.0 mole) of ethylenediamine heated at 80°. The solution was stirred at 80° overnight and then the excess amine was distilled in vacuo. The residue was triturated with i-PrOH to yield 32 g. of crude product. This material was dissolved in water, basified with dilute NaOH and the solution extracted with CH$_2$Cl$_2$. The combined extracts were dried (K$_2$CO$_3$) and concentrated in vacuo to an oil. The latter was distilled and the material boiling at 93°–95°/0.06 mm Hg was collected to yield 14.5 g. of the desired product, the identity of which was confirmed by examination of the NMR spectrum.

Procedure 91.

1-[(4-CHLOROPHENYL)METHYL]-4,5-DIHYDRO-1H-IMIDAZOL-2-AMINE HYDROCHLO-

RIDE. The amine produced in Procedure 90, 14.5 g. (0.079 mole) was dissolved in 50 ml. of methanol and treated with a solution 9.1 g. (0.086 mole) of cyanogen bromide in 30 ml. of methanol in dropwise fashion. The warm solution was cooled to room temperature which resulted in the formation of a precipitate. The mixture was kept with stirring for ½ hr. and then a portion of the solvent was removed by distillation in vacuo. The solid product which separated was collected on a filter, washed with Et$_2$O, and air dried, yield 16 g., m.p. 270°–272°.

Anal. Found: C, 41.04; H, 4.48; N, 14.39. The IR and NMR spectra confirmed the identity of the product.

Procedure 92.

7-AMINO-1-[(4-CHLOROPHENYL)METHYL]-2,3-DIHYDRO-6-NITROSOIMIDAZO-[1,2-a]PYRIMIDIN-5-(1H)-ONE. The product of Procedure 91 was condensed with ethyl oximinocyanoacetate according to the method described in Procedure 1. The crude product, 1.6 g., from 2.9 g. of the product of Procedure 91, was a blue solid, m.p. 273°–275° d, recrystallized from dimethylformamide, m.p. 290°–291° d.

Anal. Found: C, 50.84; H, 3.92; N, 22.76. The IR and NMR spectra confirmed the structure.

Procedure 93.

5-[(4-CHLOROPHENYL)METHYL]-6,7-DIHYDRO-3H-IMIDAZO[1,2-a]PURIN-9(5H)-ONE. The nitroso compound of Procedure 92 was reduced with sodium dithionate in formic acid according to the method of Procedure 21. The resulting 6-formylamino compound, 1.3 g. (0.0041 mole), was suspended in 40 ml. of water containing 0.0043 mole of NaOH and the mixture was heated on the steam bath until dissolution occurred. The solution was treated with charcoal, filtered, cooled and acidified with HOAc to yield the desired product, 0.85 g., recrystallized from MeOH, yield 0.60 g., hemihydrate m.p. 314°–316° d.

Anal. Found: C, 54.06; H, 3.98; N, 22.62. NMR (DMSO-d$_6$): 3.63 (2, m); 4.19 (2, m); 4.56 (2, s); 7.40 (4, s); 7.87 (1, s); 13.15 (1, bs). IR: 780, 1290, 1350, 1450, 1490, 1520, 1630, and 3100.

Procedure 94.

4-[(4-CHLOROPHENYL)METHYL]-4,6,7,9-TETRAHYDRO-1,5-DIMETHYL-9-OXO-1H-IMIDAZO[1,2-a]PURINIUM IODIDE. A suspension of the product of Procedure 67 (1.6 g., 0.005 mole) in acetone (25 ml.) was refluxed overnight with iodomethane (0.7 g., 0.005 mole). Additional iodomethane (0.35 g., 0.0025 mole) was added, and refluxing was continued for 24 hr. The insolubles were collected to give 1.6 g. Recrystallization from MeOH gave analytically pure product 1.1 g., m.p. 188.5°–189.5°.

Anal. Found: C, 41.99; H, 3.72; N, 15.24. NMR (DMSO-d$_6$) 3.18 (3, s); 3.28 (1, bs); 3.95 (3, s); 4.09 (2, s); 5.64 (2, s); 7.44 (4, s); 8.19 (1, s). IR: 750, 1300, 1410, 1595, 1630, 1715, and 3050.

Procedure 95.

6,7-DIHYDRO-1,5-DIMETHYL-1H-IMIDAZO[1,2-a]-PURIN-9(5H)-ONE (Formula XV, R$^{11}$, and R$^{15}$=CH$_3$). A mixture of the quaternary salt of Procedure 94 and 10% palladium on carbon in abs. EtOH is subjected to hydrogenolysis at a pressure of about 50 psig. The spent catalyst is removed by filtration, the filtrate concentrated in vacuo, and the residue dissolved in water. Treatment with concentrated NH$_4$OH liberates the free base which is collected and dried.

Procedure 96.

4-[(4-CHLOROPHENYL)METHYL]-6,7-DIHYDRO-9-IMINO-3H,4H-IMIDAZO[2',1':5,6]-v-TRIAZOLO[4,5-d]PYRIMIDINE. The product of Procedure 25 is converted to the corresponding 9-thione and 9-(methylthio) compounds and thence to the desired product by the method of Procedures 75, 76, and 77.

Procedure 97.

4-[(4-CHLOROPHENYL)METHYL]-2,3,6,7-TETRAHYDRO-2-THIOXO-1H-IMIDAZO[1,2-a]PURIN-9(4H)-ONE MONOHYDRATE. A mixture of 5% palladium on carbon (1 g.) and 2.0 g. (0.0066 mole) of the product of Procedure 1 in MeOH (50 ml.) was hydrogenated until H$_2$ uptake ceased. The catalyst was removed and carbon disulfide (0.5 g. 0.0066 mole) was added. The solution was refluxed for 4 hrs. and stirred at room temperature for 16 hrs. The mixture was concentrated in vacuo and the residue suspended in H$_2$O (50 ml.), and refluxed for 6 hrs., cooled, and 1.55 g. of solid collected by filtration. The solid was dissolved in dil. NaOH, treated with activated carbon, and reprecipitated with HOAc to give 1.18 g. of product, m.p. 232°–235°.

NMR (DMSO-d$_6$+CF$_3$COOH): 4.09 (2, m); 4.30 (2, m); 5.35 (2, s); 7.40 (4, m). IR: 750, 1300, 1440, 1500, 1630 and 1710.

Procedure 98.

4-[(4-CHLOROPHENYL)METHYL]-6,7-DIHYDRO-2-METHYLTHIO-3H-IMIDAZO[1,2-a]PURIN-9(5H)-ONE. To a solution of the product of Procedure 97 (2.4 g., 0.0068 mole) in 0.1N NaOH (85 ml.), iodomethane (1.94 g., 0.0136 mole) was added and the mixture stirred at room temperature for 16 hrs. The insolubles were collected and recrystallized from methoxyethanol to give 1.3 g. of product, m.p. 296°–297°.

Anal. Found: C, 51.57; H, 3.98; N, 20.18. NMR (DMSO-d$_6$) 2.60 (3, s); 3.84 (4, m); 5.03 (2, s); 7.37 (4, m). IR: 750, 1290, 1450, 1490, 1540, 1620, 1685, 3060, and 3130.

Procedure 99.

7-AMINO-8-[(4-CHLOROPHENYL)METHYL]-2,3-DIHYDRO-2-METHYL-6-NITROSOIMIDAZO[1,2-a]PYRIMIDIN-5(8H)-ONE. To a stirred suspension of 4-methylimidazoline-2-thione (45.0 g., 0.387 mole; purified by water recrystallization) in ethanol (200 ml., dried over 4A molecular sieve), methyl iodide (54.9 g., 0.387 mole) was added dropwise. The reaction was stirred at room temperature for 4 hr. during which time the solid dissolved. To this solution 4-chlorobenzylamine (54.8 g., 0.387 mole) was added and the solution was heated at reflux for 16 hrs. This solution was added while hot to a solution of sodium (35.6 g., 1.55 gram atom) in ethanol (900 ml., dried over 4A molecular sieve), and ethyl oximinocyanoacetate (5.50 g., 0.387 mole) was added in portions. The mixture was refluxed for 3 hrs. and concentrated in vacuo. Water (600 ml.) was added to the residue and the solution neutralized with HOAc. The orange precipitate was collected, washed with CH$_3$CN and Et$_2$O to give 95.6 g. (77%) orange solid, m.p. 222°–223° (dec.).

Procedure 100.

4-[(4-CHLOROPHENYL)METHYL]-6,7-DIHYDRO-6-METHYL-3H-IMIDAZO[1,2-a]PURIN-9(4H)-ONE. The nitroso compound of Procedure 99 was reduced with sodium dithionate in formic acid according to the method of Procedure 21. The resulting 7-amino-8-[(4-chlorophenyl)methyl]-2,3-dihydro-6-formylamino-2-methylimidazo-[1,2-a]pyrimidin-5(8H)-one, 185 g., (0.54 mole) was then dissolved with heating in 1 l. of 0.6 N NaOH, the solution clarified by filtration, the filtrate acidified with acetic acid, and allowed to cool resulting in precipitation of the desired product, yield 71.7 g., recrystallized from ethylene glycol monomethyl ether/(iPr)₂O, m.p. 259°–260.5°.

Anal. Found: C, 57.28; H, 4.37; N, 22.17. NMR (DMSO-d₆) 1.19 (3, d, 6.0 Hz); 3.45 (1, m); 4.07 (2, m); 5.06 (2, s); 7.38 (4, m); 7.82 (1, s). IR: 760, 1430, 1490, 1550, 1620, 1685, 2960, and 3120.

Procedure 101.

4-[(4-CHLOROPHENYL)METHYL]-6,7-DIHYDRO-2,6-DIMETHYL-3H-IMIDAZO[1,2-a]PURIN-9(4H)-ONE. The product of Procedure 99 was reduced with sodium dithionate in formic acid according to the method of Procedure 21. The resulting 7-amino-4-[(4-chlorophenyl)methyl]-2,3-dihydro-6-formylamino-2-methylimidazo[1,2-a]pyrimidin-5-(8H)-one, 3.5 g. (0.0104 mole) in 7 ml. of pyridine and 7 ml. of acetic anhydride was refluxed for three 3 hrs. during which the mixture foamed and turned dark. The mixture was allowed to cool to room temperature and diluted with acetonitrile resulting in the formation of a white precipitate which was collected. Recrystallized from iPROH/MeOH, yield 800 mg., m.p. 290°–291° C.

Anal. Found: C, 58.12; H, 5.01; N, 21.08. NMR (DMSO-d₆): 1.17 (3, d, 6.0 Hz); 2.29 (3, s); 3.40 (1, m); 4.04 (2, m); 5.00 (2, s); 7.35 (4, s); 12.90 (1, bs). IR: 755, 1330, 1500, 1620, 1680, 2960, and 3160.

Procedure 102.

4-[(4-CHLOROPHENYL)METHYL]-6,7-DIHYDRO-1,6-DIMETHYL-1H-IMIDAZO[1,2-a]PURIN-9(4H)-ONE MONOHYDRATE. The product of Procedure 100, 27.5 g. (0.087 mole) was dissolved in 250 ml. of water containing 0.1 mole of sodium hydroxide. 50 ml. of ethanol was added followed by 28 g. (0.197 mole) of iodomethane. The mixture was stirred at room temperature for 3 days after which the product was collected by filtration and air dried. The damp solid was recrystallized from CH₃CN/iPr₂O, yield 19.3 g., m.p. 147°–148°.

Anal. Found: C, 55.40; H, 5.08; N, 20.27; H₂O 5.53. NMR (DMSO-d₆) 1.18 (3, d, 6.0 Hz); 3.28 (1, s); 3.42 (1, m); 3.80 (3, s); 4.07 (2, m); 5.01 (2, s); 7.37 (4, s); 7.79 (1,s). IR: 755, 1340, 1490, 1580, 1630, 1680, and 2960.

Procedure 103.

7-AMINO-8-[(4-CHLOROPHENYL)METHYL]-2,3-DIHYDRO-2,2-DIMETHYL-6-NITROSOIMIDAZO[1,2-a]-PYRIMIDIN-5(8H)-ONE. 4,4-Dimethylimidazoline-2-thione was prepared by adding a solution of 50 g. of 1,2-diamino-2-methylpropane in 35 ml. of methylene chloride dropwise with stirring to a solution of 43 g. of carbon disulfide in 200 ml. of methylene chloride during about 3 hrs. The product formed as a white precipitate immediately on mixing of the two solutions. The solvent was removed by distillation in vacuo and replaced with water, and the mixture was refluxed for 7 hrs. It was concentrated to one-half the original volume, clarified by filtration while hot, and the product allowed to crystallize from the filtrate, yield 60.6 g., m.p. 114°–115°. A portion of this material, 43.9 g., (0.337 mole), was treated with 47.9 g. (0.337 mole) of methyl iodide in 400 ml. of ethanol. The methyl iodide was added by dropwise addition. The mixture was then concentrated in vacuo to an oil which was mixed with i-Pr₂O to induce crystallization resulting in the formation of a light yellow solid, yield 90.7 g. (99%), of 2-methylthio-4,4-dimethyl-2-imidazoline hydroiodide. A portion of this material, 27.2 g. (0.1 mole), and 14.1 g. (0.1 mole) of p-chlorobenzylamine were dissolved in 100 ml. of abs. EtOH and added to a solution of 9.0 g. (0.4 mole) of sodium in 400 ml. of abs. EtOH at the reflux temperature. The solution was stirred for 10 min. and 14.2 g. (0.1 mole) of ethyl oximinocyanoacetate was added in portions during a period of about 5 min. The reaction solution became clear and bright yellow in color. It was refluxed for 4½ hrs. and then concentrated in vacuo to yield an oily solid. The latter was dissolved in water and treated with acetic acid resulting in formation of the desired product as a red precipitate which was collected and air dried, m.p. 214°–215°, yield 16.7 g. (50%).

Procedure 104.

4-[(4-CHLOROPHENYL)METHYL]-6,7-DIHYDRO-6,6-DIMETHYL-3H-IMIDAZO[1,2-a]PURIN-9(4H)-ONE. The nitroso compound produced in Procedure 103 was reduced to the corresponding 6-formylamino compound and the latter cyclized all according to the method of Procedure 100 to yield the desired product, m.p. 222°–223° after recrystallization from acetonitrile, yield 30%.

Anal. Found: C, 58.57; H, 4.83; N, 21.10. NMR (DMSO-d₆) 1.23 (6, s); 3.65 (2, s); 5.04 (2, s); 7.38 (4, m); 7.80 (1, s); 13.20 (1, bs). IR: 760, 1430, 1490, 1550, 1585, 1625, 1690, 2965, and 3120.

Procedure 105.

7-AMINO-8-[(4-CHLOROPHENYL)METHYL]-2,3-DIHYDRO-2,3-DIMETHYL-6-NITROSOIMIDAZO-[1,2-a]PYRIMIDIN-5(8H)-ONE. 4,5-Dimethylimidazoline-2-thione was prepared by reaction of 2,3-diaminobutane dihydrochloride with carbon disulfide as described in Procedure 103. The resulting thione was then caused to react with methyl iodide and thence with p-chlorobenzylamine and ethyl oximinoacetate to yield the desired product according to the method of Procedure 99. After decanting the aqueous acetic acid from which the crude product had been precipitated, the solid was washed with isopropanol and air dried yielding a pink solid, m.p. 224°–226° B, yield 43%. The identity of the product was confirmed by examination of the NMR spectrum. Th 1,2-diaminobutane required as starting material was prepared by hydrogenation of dimethylglyoxim over a platinum catalyst at atmospheric pressure, m.p. 225°–235° C.

Procedure 106.

4-[(4-CHLOROPHENYL)METHYL]-6,7-DIHYDRO-6,7-DIMETHYL-3H-IMIDAZO[1,2-a]PURIN-9(4H)-ONE. The nitroso compound of Procedure 105 was reduced with sodium dithionate in formic acid according to the method of Procedure 21 yielding the corresponding 6-formylamino compound which was recovered by concentrating the reaction mixture in vacuo to a gummy foam. The residue was taken up in dilute aqueous sodium hydroxide solution (approximately 1.5N) and the solution heated on the steam bath for 2 hrs. An oily residue remained which was dissolved by the addition of further portion of sodium hydroxide solution. A small amount of residual tar was removed by decanting the solution and the orange filtrate (volume approximately 3.5 liters) was acidified with acetic acid resulting in the precipitation of the desired product as a brown solid, m.p. 200°–220° C. This material was recrystallized from 1.4 l. of 95% ethanol and air dried yielding 36.7 g. of product, m.p. 252°–254° C. It was again recrystallized from 95% ethanol, 1 l., yielding a pale pink solid which was air dried, yield 26 g., m.p. 259°–260° C. TLC using 9:1 $CH_2Cl_2$/MeOH for development revealed one spot corresponding to the more polar of the two isomers, determined to be the trans-isomer.

Anal. Found: C, 58.01; H, 4.84; N, 21.35. NMR (DMSO-$d_6$): 1.20 (6, m); 3.50–4.50 (2, m); 5.04 (2, s); 7.36 (4, m); 7.80 (1, s). IR: 760, 1430, 1550, 1590, 1625, 1690, 2970, and 3120.

The ethanolic filtrate from the first of the foregoing recrystallizations was concentrated in vacuo to yield a red-brown solid, weight 52 g. A small portion of this material after recrystallization from acetonitrile gave a tan solid, m.p. 210°–215° which was shown by TLC using the above system to contain about equal portions of the two isomers. Five grams of the red-brown solid was chromatographed on a silica column containing 400 g. of silica and eluted with methylene chloride containing 5% by volume of methanol. Twenty milliliter factions were collected. Fractions 150–175 yielded 0.6 g. of the pure cis-isomer on evaporation, m.p. 248°–249° C. Recrystallized from i-PrOH, m.p. 247°–248°.

Anal. Found: C, 58.12; H, 4.94; N, 21.06. Using 5% methanol in methylene chloride on silica, the pure cis-isomer exhibited $R_f$ 0.3.

Procedures 107–111.

By substitution of the appropriate amine ($R^{14}NH_2$) in one of the methods of Procedures 1, 30 with 31, or 99, the appropriate 7-amino-8-$R^{14}$-2,3-dihydro-6-nitrosoimidazo[1,2-a]-pyrimidin-5(8$\underline{H}$)-one is produced. The latter is then converted to any of the products shown in the addendum to Table IV which follows by the method of Procedure 100 or by the method of Procedure 63 modified by substitution of the appropriate carboxylic acid anhydride ($R^{12}CO)_2O$.

Addendum to Table IV
Procedures 107–111
Formula XX
$Q = O$, $n = 1$, $R^6$, $R^7$, $R^{11}$ and $R^{16} = H$

| Proc. No | $R^{12}$ | $R^{14}$ | m.p. °C. (Corr) | Method | Recryst. Solvent | Elemental Analysis | NMR | IR |
|---|---|---|---|---|---|---|---|---|
| 107 | $CH_3CH_2$ | $(CH_3)_2CHCH_2$ | 242–243 | Proc. 63 | $CH_3CN$ | C, 59.49 H, 7.49 N, 26.71 | ($CDCl_3$): 0.96 (6,d, 7.0 Hz); 1.38 (3,t, 7.6 Hz); 2.42 (1,m); 2.82 (2,q, 7.6 Hz); 3.85 (2,d, 7.9 Hz); 4.01 (4,m) | 750, 1290, 1510, 1560, 1610, 1630, 1630, 1695, 2960, 3040 |
| 108 | $(CH_3)_2CH$ | 2-phenoxy-ethyl | 167.5–170.5 | Proc. 63 | i-PrOH | C, 63.35 H, 6.28 N, 20.79 | (DMSO-$d_6$): 1.25 (6,d, 7.0 Hz); 2.99 (1,septet, 7.0 Hz); 3.84 (4,m); 4.27 (4,m); 7.10 (5,m); 12.85 (1,bs) | 755, 1240, 1500, 1590, 1620, 1680, 2960, 3160 |
| 109* | H | $(CH_3)_2CHCH_2$ | 201–202 | Proc. 100 | $CH_3CN$ | C, 57.95 H, 6.91 N, 28.42 | ($CDCl_3$): 0.96 (6,d, 7.8 Hz); 1.32 (3,d 6.1 Hz); 2.42 (1,m); 3.64 (1,m); 3.87 (2,d, 7.6 Hz); 4.23 (2,m); 7.65 (1,s) | 760, 1430, 1550, 1590, 1625, 1690, 2960, 3130 |
| 110 | $CH_3$ | 2-methyl-2-phenoxyethyl | 215–217 | Proc. 63 | i-PrOH | C, 62.59 H, 5.88 N, 21.28 | (DMSO-$d_6$): 1.28 (3,d, 6.2 Hz) 2.31 (3,s); 3.79 (4,m); 4.05 (2,m); 5.00 (1,m); 7.02 (5,m) | 750, 1240, 1510, 1590, 1625, 1690, 3050, 3160 |
| 111 | H | 2-methyl-2-phenoxyethyl | 244–246 | Proc. 100 | i-PrOH | C, 61.73 H, 5.49 N, 22.55 | (DMSO-$d_6$): 1.29 (3,d, 6.1 Hz); 3.82 (4,m); 4.07 (2,m); 5.02 (1,m); 7.01 (5,m) 7.81 (1,s) | 760, 1230, 1490, 1550, 1580, 1610, 1685, 2600, 2880, 3090 |

*Procedure 109. $R^6$ is 6-$CH_3$. 7-Amino-8-(2-methylpropyl)-2,3-dihydro-2-methyl-6-nitrosoimidazo[1,2-a]pyrimidin-5(8H)-one required as starting material was produced by the method of Procedure 99 by substitution of isobutylamine for 4-chlorobenzylamine.

Procedures 112–117.

Various 1-$R^{16}$,7-dihydro-(1$\underline{H}$)imidazo[1,2-a]purin-9(4$\underline{H}$)-ones were prepared by application of the method of Procedure 102 to the appropriate $R^{11}X$ starting material in combination with one of the foregoing products as shown in Table IX.

TABLE IX

Procedures 112–117
Formula XX
$Q = O$, $R^{14} = $ p-Clbenzyl; $R^6$, $R^7$, $R^{16} = H$, $n = 1$

| Proc. No | $R^{11}$ | $R^{12}$ | m.p. °C. (Corr) | Starting Material | Recryst. Solvent | Elemental Analysis | NMR | IR |
|---|---|---|---|---|---|---|---|---|
| 112 | $CH_3$ | $CH_3$ | 170–172 | Proc. 15 | i-PrOH | C, 59.22 H, 5.31 N, 20.22 | (DMSO-$d_6$): 1.17 (3,d, 6.0 Hz) 2.32 (3,s); 3.41 (1,m); 3.74 (3,s); 4.06 (2,m); 5.00 | 750, 800, 1330, 1450, 1490, 1585, 1640, 1690, 2970 |

TABLE IX-continued

Procedures 112–117
Formula XX
Q = O, R$^{14}$ = p-Clbenzyl; R$^6$, R$^7$, R$^{16}$ = H, n = 1

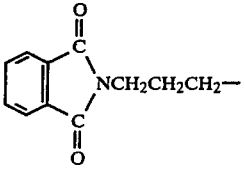

| Proc. No | R$^{11}$ | R$^{12}$ | m.p. °C. (Corr) | Starting Material | Recryst. Solvent | Elemental Analysis | NMR | IR |
|---|---|---|---|---|---|---|---|---|
| 113* | CH$_3$ | CH$_3$ | 133–135 | Proc. 63 | i-Pr$_2$O | C, 58.89<br>H, 7.40<br>N, 26.30 | (CDCl$_3$): (2,s); 7.35 (4,s)<br>0.94 (6,d, 7.0 Hz)<br>2.38 (3,s); 2.38 (3,s);<br>2.39<br>(1,m); 3.78 (2,m);<br>3.82 (3,s);<br>3.95 (4,m) | 705, 1465, 1580,<br>1630, 1690, 2960 |
| 114 | —CO$_2$C$_2$H$_5$ | H | 167–170 | Proc. 4 | CH$_3$CN | C, 54.53<br>H, 4.27<br>N, 19.05 | (DMSO-d$_6$):<br>1.36 (3,t, 7.2 Hz)<br>3.83 (4,m)<br>4.42 (2,q, 7.2 Hz)<br>5.05 (2,s); 7.36<br>(4,s); 8.47 (1,s) | 760, 1250, 1380,<br>1585, 1650 1690<br>1760, 1790, 3140, |
| 115 | (phthalimido-propyl, see structure above) | H | 187–188 | Proc. 4 | MeO(CH$_2$)$_2$OH | C, 61.20<br>H, 4.32<br>N, 16.86 | (DMSO-d$_6$);<br>2.14 (2,m)<br>3.57 (2,t, 6.4 Hz)<br>3.78 (4,m); 4.20<br>(2,m); 4.95 (2,s);<br>7.34 (4,m); 7.82<br>(5,m) | 720, 760, 1400,<br>1470, 1580, 1640,<br>1680, 1720, 1770,<br>2950 |
| 116* | H$_2$NCH$_2$CH$_2$CH$_2$— | H | 239–240 | Proc. 115 | EtOH | C, 53.05<br>H, 5.04<br>N, 11.90 | (DMSO-d$_6$):<br>2.19 (2,m); 2.28<br>(6,s); 2.82 (2,m);<br>3.40 (2,m); 4.20<br>(4,m); 5.33 (2,s);<br>7.09 (4,m); 7.48<br>(8,m); 7.80 (3,bs);<br>8.25 (1,s) | 820, 1010, 1030,<br>1160, 1220, 1490,<br>1600, 1650, 1730,<br>3020 |
| 117 | CH$_3$ | CH$_3$ | 228.5–229.5 | Proc. 15 | EtOH | C, 58.60<br>H, 4.84<br>N, 21.47 | (CDCl$_3$):<br>2.38 (3,s); 3.81<br>(3,s); 3.95 (4,m);<br>5.08 (2,s); 7.31<br>(4,m) | 755, 1430, 1490,<br>1585, 1635, 1690,<br>2960 |

*Proc. 113: R$^{14}$ = 2-methylpropyl
*Procedure 116. The product of Procedure 115, 0.5 g. (0.001 mole), was suspended in 30 ml. of abs. EtOH, and 0.25 g. (0.005 mole) of hydrazine hydrate was added. The mixture was refluxed for 1.5 hrs. When first heated, the starting material dissolved. A white precipitate formed during the heating period. The reaction mixture was cooled, clarified by filtration, and the solvent distilled from the filtrate in vacuo. The oil was dissolved in methanol and the solution acidified with p-toluenesulfonic acid. Distillation of the solvent in vacuo left a residue which was washed with Et$_2$O and triturated with Me$_2$CO yielding 0.5 g. of the desired product as the ditosylate salt. This material was recrystallized from 95% EtOH, yield 0.42 g. Melting point and analytical data appear in the table.

Procedure 118.

7-AMINO-2,3-DIHYDRO-1-(2-METHYL-PROPYL)-6-NITROSOIMIDAZO[1,2-a]PYRIMIDIN-5(1H)-ONE. Methyl isobutyrate and ethylenediamine in a molar ratio of 1:3 were heated in a closed pressure vessel at 100° for 62 hrs. The mixture was cooled, clarified by filtration, and the excess ethylenediamine removed from the filtrate by distillation in vacuo. The residue was distilled, boiling point 115°–117°/0.9 mm Hg to yield N-isobutyrylethylenediamine whose identity was confirmed by examination of the NMR and IR spectra. The latter, 15 g., was suspended in 200 ml. of dry THF and a solution of 20 g. (ca. 0.5 mole) of lithium aluminum hydride in 200 ml. of dry THF was added dropwise. The mixture was refluxed for 23 hrs., the excess lithium aluminum hydride destroyed by hydrolysis. The insoluble material was removed by filtration, and the filtrate concentrated in vacuo to yield N-(2-methylpropyl)ethylenediamine as an oil, yield 37 g. The identity of the product was confirmed by examination of the NMR spectrum, and 5.8 g. (0.05 mole) thereof was then dissolved in 20 ml. of MeOH and a solution of 5.8 g. (0.055 mole) of cyanogen bromide in MeOH was added in dropwise fashion with cooling. The mixture was stirred for ½ hr. and then concentrated in vacuo to an oil. The latter was dissolved in methylene chloride and again concentrated in vacuo to aid in removal of last traces of MeOH. The NMR spectrum of the residue, an oil, confirmed the structure 1-(2-methylpropyl)-1H-imidazo-2-amine hydrobromide. This material was then condensed with ethyl oximinocyanoacetate substantially according to the method described in Procedure 1. The product was recovered by distillation of the solvent from the reaction mixture in vacuo. The residue was dissolved in water and acidified with acetic acid. The precipitate that formed was collected and air dried. The damp solid was recrystallized from methanol/ethanol, m.p. 242.5°–243.5° d.

Anal. Found: C, 48.40; H, 6.42; N, 28.23; H$_2$O, 3.27. The identity of the product was further confirmed by examination of the IR and NMR spectra.

Procedure 119.

6,7-DIHYDRO-5-(2-METHYLPROPYL)-3H-IMIDAZO-[1,2-a]PURIN-9(5H)-ONE. The nitroso compound produced in Procedure 118 was converted to the desired product by the method of Procedure 100, recrystallized from ethanol, m.p. 233°–237° d.

Anal. Found: C, 56.44; H, 6.46; N, 29.96. NMR (DMSO-d$_6$): 0.92 (6, d, 7.0 Hz); 2.01 (1, m); 3.16 (2, d, 7.8 Hz); 3.73 (2, m); 4.18 (2, m); 7.82 (1, s). IR: 775, 1290, 1350, 1440, 1490, 1525, 1600, 1630, and 2950.

Procedures 120-122.

The method of Procedure 77 modified by the substitution of the various amines shown in Table X for ammonia yielded the indicated products.

ous NaOH and precipitating with HOAc to yield 0.25 g. of product, m.p. 291°-293° (dec.).

Anal. Found: C, 56.10; H, 3.38; N, 23.68. NMR (DMSO-$d_6$): 5.54 (2, s); 7.15 (1, d, 2.0 Hz); 7.39 (4, m); 7.66 (1, d, 2.0 Hz); 8.22 (1, s). IR: 690, 760, 1240, 1365, 1490, 1585, 1630, 1696. and

TABLE X

Procedures 120-122
Formula XX
$Q = R^{10}N$, $R^{14} = $ p-Clbenzyl, $n = 1$, $R^{11}$, $R^{12}$, $R^6$, $R^7$, $R^{16} = H$

| Proc. No | Amine | $R^{10}$ | m.p. °C. (corr.) | Recryst. Solvent | Elemental Analysis | NMR | IR |
|---|---|---|---|---|---|---|---|
| 120 | 2-methylpropylamine | $(CH_3)CHCH_2$ | | I-PrOAc | C, 60.37 H, 6.06 N, 23.39 | (DMSO-$d_6$): 0.92 (6,d, 7.0 Hz) 1.93 (1,m); 3.90 (6,m); 5.04 (2,s); 7.27 (1,s); 7.38 (4,m); 7.85 (1,bs) | 750, 1300, 1490, 1535, 1600, 1665, 2960 |
| 121 | N,N—Dimethyl-triethylenediamine | $(CH_3)_2NCH_2CH_2CH_2$ | | i-PrOAc | C, 58.21 H, 6.24 N, 24.88 | (DMSO-$d_6$): 1.78 (2,m); 2.16 (3,s); 2.34 (2,t) 6.9 Hz); 3.88 (4,m); 4.03 (2,t, 6.9 Hz) 5.03 (2,s); 6.40 (1,bs); 7.29 (1,s); 7.37 (4,m) | 780, 1290, 1490, 1530, 1600, 1660, 2960, 3230 |
| 122 | cyclopropylamine | | | EtOH | C, 45.35 H, 5.15 N, 18.56 | (DMSO-$d_6$): 1.10 (4,m); 3.49 (1,m); 4.12 (2,m); 4.51 (2,m); 5.68 (2,s); 7.10 (3,bs); 7.50 (4,m); 8.51 (1,s) | 745, 1295, 1380, 1490, 1560, 1625, 1690, 3350 |

Procedure 123.

4-[2-(4-CHLOROPHENOXY)ETHYL]-4,6,7,9-TETRAHYDRO-5-METHYL-9-OXO-3H-IMIDAZO[1,2-a]PURINIUM IODIDE. The product of Procedure 57, 0.9 g. (0.0027 mole), was suspended in a mixture of 10 ml. of acetonitrile and 5 ml. of methyl iodide. The suspension was heated to reflux and 2 ml. of dimethylformamide was added resulting in dissolution of all insoluble material. The solution was heated overnight at reflux, cooled to room temperature, and 15 ml. of ether was added resulting in separation of the product as an oil. The solvent was decanted from the oil and the oil was triturated with acetone resulting in solidification thereof. The yellow solid was collected by filtration, weight 0.55 g. (12% yield) m.p. 185.0°-196.0° (corr.). This material was a hydrated dimethylformamide solvate of the desired product.

Anal. Found: C, 38.96; H, 3.75; N, 13.92. NMR (DMSO-$d_6$): 3.20 (1, s); 3.58 (1, s); 3.96 (3, s); 4.18 (4, m); 4.50 (4, m); 7.21 (4, m); 8.39 (1, s). IR: 760, 840, 1245, 1495, 1600, 1640, 1725 and 3080.

Formula XX
$R^{16}$ Is A Double Bond

Procedure 124.

4-[(4-CHLOROPHENYL)METHYL]-3H-IMIDAZO[1,2-a]PURIN-9(4H)-ONE. A suspension of the product of Procedure 3, 5 g., (0.017 mole), and 13 g. of activated $MnO_2$ in 500 ml. of xylene was refluxed for 5 days. The mixture was clarified by filtration, the filtrate concentrated in vacuo, and the residue extracted with 700 ml. acetone. The acetone was concentrated in vacuo and the residue triturated with iPrOH to give 0.4 g. of solid. The product was purified by first recrystallizing from EtOH, and then by dissolving in dilute aque- Formula XX
$R^{12}$ is $CH_3SO_2$, or $CH_3SO$ Procedure 125.

4-[(4-CHLOROPHENYL)METHYL]-6,7-DIHYDRO-2-(METHYLSULFONYL)-3H-IMIDAZO[1,2-a]PURIN-9(5H)-ONE. To a mixture of 1.0 g. (0.0029 mole) of the product of Procedure 98 in 40 ml. of $CHCl_3$, 0.04 g. (0.006 mole) of m-chloroperoxybenzoic acid was added in portions and the mixture was refluxed for 1 hr. Another 0.5 g. of the peracid was added and refluxing was continued for another 1 hr. The mixture was stirred overnight, and the precipitated product was collected to give 0.95 g. thereof. Recrystallization from methoxyethanol gave 0.5 g. of white crystals, m.p. 282°-283.5°.

Anal. Found: C, 47.36; H, 3.76; N, 18.26. NMR (DMSO-$d_6$): 3.13 (3, s); 3.95 (2, m); 4.18 (2, m); 5.30 (2, s); 7.41 (4, s). IR: 760, 1120, 1300, 1490, 1570, 1630, and 1710. By using 0.0029 mole of m-chloroperoxybenzoic acid in Procedure 125, 4-[(4-chlorophenyl)methyl]-6,7-dihydro-2-(methylsulfinyl)-3H-imidazo[1,2-a]purin-9(5H)-one is produced.

Formulas XI and XXII

Procedures 126-128

Triazoles

The method of Procedure 25 was employed to produce the compounds of Procedures 126-127.

Procedure 126.

5-[(4-CHLOROPHENYL)METHYL]-6,7-DIHYDRO-3H-IMIDAZO[2', 1':5,6]-v-TRIAZOLO]4,5-d]PYRIMIDIN-9(5H)-ONE HYDROCHLORIDE. The product of Procedure 92 was used as starting material. Product was recrystallized from MeOH, yield 60%, m.p. 237.5°–239.5° (dec.).

Anal. Found: C, 46.19; H, 3.54; N, 24.83. NMR (DMSO-$d_6$): 3.89 (2, m); 4.30 (2, m); 4.89 (2, s); 7.45 (4, s); 14.10 (1, bs). IR: 700, 1300, 1500, 1580, 1610, 1660, 1750, and 2720.

Procedure 127.

6,7-DIHYDRO-4-(2-METHYLPROPYL)-3H-IMIDAZO[2',1': 5,6]-v-TRIAZOLO[4,5-d]PYRIMIDIN-9(4H)-ONE HYDROCHLORIDE. The intermediate nitroso compound produced in Procedure 13 was used as starting material. The product was recrystallized from iPrOH, yield 93%, m.p. 288°–290°.

Anal. Found: C, 44.28; H, 5.74; N, 31.02. NMR (DMSO-$d_6$): 0.99 (6, d, 6.8 Hz); 2.20 (1, m); 4.10 (6, m). IR: 770, 1315, 1390, 1580, 1660, 1740, 1750, 2800, and 2960.

Procedure 128.

4-[(4-CHLOROPHENYL)METHYL]-6,7-DIHYDRO-1-METHYL-1H-IMIDAZO[2', 1':5,6]-v-TRIAZOLO[4,5-d]PYRIMIDIN-9(4H)-ONE. A suspension of the product of Procedure 25 (1.4 g., 0.004 mole) and NaH (0.25 g., 0.006 mole, 57% in oil) in THF (40 ml.) was stirred until solution occurred. Iodomethane (1.1 g., 0.008 mole) was added and the mixture heated at 50° overnight. The mixture was concentrated in vacuo and the residue triturated with $H_2O$ to give 0.5 g. of solid. Recrystallization from EtOH gave 0.43 g. of product, m.p. 209°–210°.

Anal. Found: C, 52.84; H, 4.08; N, 26.50. NMR (DMSO-$d_6$): 3.89 (4, m); 4.14 (3, s); 5.00 (2, s); 7.37 (4, s). IR: 770, 1340, 1490, 1580, 1590, 1650, 1710, and 2960.

Procedure 129.

4-[(4-CHLOROPHENYL)METHYL]-6,7-DIHYDRO-2,6,6-TRIMETHYL-3H-IMIDAZO[1,2-a]PURIN-9(4H)-ONE. The nitroso compound of Procedure 103 was catalytically hydrogenated to the diamino compound and then treated with acetic anhydride according to the method of Procedure 63. There resulted from this process the mono N-acetyl derivative of 8-[(4-chlorophenyl)methyl]-6,7-diaminoimidazo[1,2-a]pyrimidin-5-one, m.p. 155°–159° after recrystallization from isopropanol and drying under vacuum.

Anal. Found: C, 56.63; H, 5.80; N, 29.90. The structure was confirmed by examination of the NMR and IR spectra. This mono N-acetyl compound was then dissolved in 1.1 molecular proportions of dilute aqueous sodium hydroxide solution with warming in the fashion described in Procedure 100 and the desired product recovered by neutralization of the resulting solution, yield 70%, recrystallized from methanol, m.p. 251°–252°, resolidify remelt 260°–261°.

Anal. Found: C, 59.20; H, 5.39; N, 20.24. NMR (DMSO-$d_6$): b 1.20 (6, s); 2.28 (3, s); 3.61 (2, s); 5.00 (2, s); 7.34 (4, s), 12.80 (1, bs). IR: 750, 1320, 1490, 1500, 1620, 1680, 2960, and 3160.

Procedure 130.

6,7-DIHYDRO-4-(2-METHYLPROPYL)-6,6-DIMETHYL-3-H-IMIDAZO[1,2-a]PURIN-9(4H)-ONE. 7-Amino-2,3-dihydro-2,2-dimethyl-8-(2-methylpropyl)-6-nitrosoimidazo[1,2-a]pyrimidin-5(8H)-one was prepared by reaction of the 2-methylthio-4,4-dimethyl-2-imidazoline hydrochloride with 2-methylpropylamine according to the method of Procedure 103 by substitution of the latter for p-chlorobenzylamine. The reaction product from this step was then condensed with ethyl oximinocyanoacetate as described in Procedure 103. The resulting nitroso compound was then reduced with sodium dithionate in formic acid and the resulting formylamino compound was cyclized with dilute aqueous sodium hydroxide according to Procedure 100.

Procedure 131.

6,7-DIHYDRO-4-(2-METHYLPROPYL)-2,6,6-TRIMETHYL-3H-IMIDAZO[1,2-a]PURIN-9(4H)-ONE. The nitroso compound produced in Procedure 130 was catalytically hydrogenated and cyclized by the treatment with acetic anhydride according to the method of Procedure 63.

BIOLOGICAL EVALUATION

Bronchodilator activity was estimated in vitro (Table XI, columns 2–5) employing the isolated guinea pig tracheal spiral. The concentration of substance required to cause relaxation of the spontaneous tonus (Spon) of the tissue as well as the contractions caused by various spasmogens, namely, acetylcholine (Ach), histamine (Hist), or barium chloride ($BaCl_2$) was measured. The values reported are $IC_{50}$ values, viz. the concentration of test compound necessary to cause 50% inhibition of the contraction. They were determined by interpolation from dose response curves prepared by plotting percent inhibition versus concentration for various concentrations of the test compounds in the test solution.

Bronchodilator activity in vivo (Table XI, column 6) was estimated by determining the dose of test compound required to inhibit methacholine-induced bronchospasm in the rat. The percentage figures represent the percent inhibition at the dose of test compound shown in parentheses. Otherwise, the value given is the dose in mg./kg. of body weight required to cause 50% inhibition of the bronchospasm ($ED_{50}$), the values having been determined by interpolation from dose response curves. For this test, pulmonary ventilation pressure (PVP) was the parameter measured using anesthetized animals. The test compound was administered intraduodenally followed at 5, 15, and 30-minute intervals by that intravenous dose of methacholine which had previously been determined to cause a 50% reduction in PVP. Percent inhibition then was the degree to which the test compound inhibited the reduction in PVP resulting from the methacholine infusion.

Antiallergy activity in terms of ability to inhibit the immediate hypersensitivity reaction was measured by means of the passive cutaneous anaphylaxis reaction (PCA) in the rat (Table XI, column 7). The animals were passively sensitized by the intradermal injection of rat reagenic antiserum at various locations on the shaved back skin and 48 hours later the test drug was administered. This was followed by challenge at a predetermined interval, usually 15 minutes, by intravenous injection of egg albumin and Evans' blue dye. The dermal reaction at the sensitized site was evaluated and scored by measuring the diameter of the spot generated at the sensitized intradermal injection site. The values reported in the table are either $ED_{50}$ values for the test compound in terms of mg./kg. of body weight administered orally, or percent inhibition of the dose specified in parentheses. "I" signifies inactive at the specified dose.

Antiallergy/bronchodilator studies (Table XI, column 8) were also conducted using rats which were actively sensitized with egg albumin and B. pertussis vaccine as for preparation of the reagenic antisera in the PCA test. Fifteen days following sensitization, the animals were prepared for measurement of PVP as for the methacholineinduced bronchospasm test, and changes in PVP in response to a standardized challenge of egg albumin following treatment with test drug were measured. The values reported in the table are $ED_{50}$ values in terms of mg./kg. of body weight for the test compound administered orally.

TABLE XI

| (1) Test Compound Proc. No. | (2) Spon | (3) Ach | (4) Hist | (5) BaCl$_2$ | (6) Methacholine Bronchospasm | (7) PCA* | (8) Allergic Bronchospasm |
|---|---|---|---|---|---|---|---|
| Theophylline | 18.5 | 19.3 | 12.1 | 41.5 | 19.2 | 41.5 | 22.4 |
| 3 | 11.4 | 26 | 3 | 35 | 5.2 | 33.7 | 2.9 |
| 5 | 12.5 | — | — | — | 64% (10) | 43% (50) | — |
| 6 | 49 | — | — | — | — | 25% (50) | — |
| 7 | 12.5 | — | — | — | — | I (25) | — |
| 8 | 17.5 | — | — | — | 55.5%(10) | 29% (10) | — |
| 9 | — | — | — | — | — | I (10) | — |
| 10 | 128 | — | — | — | — | 40% (25) | — |
| 11 | 45 | — | — | — | — | 25% (10) | — |
| 12 | 50 | 4.8 | — | 86 | 2.3 | 27% (25) | — |
| 13 | 6.3 | — | — | — | 63% (10) | I (25) | — |
| 14 | 13 | — | — | — | 26% (10) | 29% (10) | — |
| 15 | 5.3 | 3.5 | 0.9 | 19.1 | 1.79 | 40% (30) | — |
| 16 | >7.0 | — | — | — | — | I (25) | — |
| 17 | 54 | — | — | — | — | 34% (25) | — |
| 20 | >200 | — | — | — | — | 46% (25) | — |
| 23 | 22.5 | — | — | — | — | I (25) | — |
| 24 | 15.5 | — | — | — | 16% (10) | I (10) | — |
| 25 | 80 | — | — | — | — | I (10) | — |
| 26 | >200 | — | — | — | — | 41% (10) | — |
| 27 | >200 | — | — | — | 30% (10) | 17.7 | — |
| 28 | 51 | 175 | — | 98 | — | I (10) | — |
| 39 | 11.3 | — | — | — | 34.7% (10) | I (25) | — |
| 44 | — | — | — | — | 0% (10) | I (10) | — |
| 46 | 3.9 | — | — | — | >30.0 | — | — |
| 47 | — | — | — | — | — | — | — |
| 54 | 24.5 | — | — | — | — | I (25) | — |
| 55 | >50 | — | — | — | — | 34.9% (25) | — |
| 56 | — | — | — | — | — | 25.0% (25) | — |
| 57 | 58.0 | — | — | — | 66% (10) | 31.7% (25) | — |
| 58 | 25.5 | 0.49 | 37.01 | 74.05 | 0.81 | 29% (25) | — |
| 59 | 10 | — | — | — | 45.8 (10) | 29% (25) | — |
| 60 | 53 | — | — | — | I (10) | I (25) | — |
| 61 | 11.5 | — | — | — | 51 (10) | 15.3 | — |
| 62 | 34.5 | — | — | — | 22 (10) | I (25) | — |
| 63 | 2.8 | 5.5 | 3.2 | 75 | 3.3 | 33.9 | 5.4 |
| 66 | 200 | — | — | — | — | — | — |
| 67 | 2.9 | — | — | — | 8.8 | 26% (25) | — |
| 74 | >200 | — | — | — | I (10) | I (25) | — |
| 75 | 5.1 | 50 | 15 | 23.5 | 21 (30) | I (25) | — |
| 76 | 8.1 | — | — | — | 21 (30) | 47% (25) | — |
| 77 | 19.8 | — | — | — | 22 (30) | — | — |
| 78 | — | — | — | — | — | — | — |
| 84 | — | — | — | — | — | — | — |
| 93 | 26.3 | — | — | — | — | — | — |
| 94 | — | — | — | — | — | — | — |
| 97 | — | — | — | — | — | — | — |
| 98 | 13.7 | — | — | — | — | — | — |
| 100 | 3.7 | 1.92 | 0.13 | 29.64 | 2.1 | 10.6 | 1.5 |
| 101 | 4.4 | 3.03 | 0.67 | 31.09 | 1.00 | 30.2 | 1.2 |
| 102 | 2.3 | 3.4 | 0.18 | 15.1 | 1.1 | 28.9 | 3.4 |
| 104 | 14.3 | 4.0 | 0.22 | 16.5 | 6.3 | 42.8 | 3.0 |
| 106 (mixed) | 2.4 | 1.6 | 0.22 | 10.8 | 3.7 | 20.3 | 3.51 |
| 106 (cis) | — | — | — | — | 3.0 | 28.5 | — |
| 106 (trans) | — | — | — | — | 5.0 | 35.5 | — |
| 107 | 16.7 | — | — | — | — | — | — |
| 108 | 41.4 | 3.3 | 47.5 | 74.4 | 4.0 | — | — |
| 109 | 14.0 | 30.8 | 1.20 | 50.2 | 4.6 | — | — |
| 110 | — | >200 | 48 | 140 | — | — | — |
| 111 | — | — | — | — | — | — | — |
| 112 | 7.9 | 104 | 8.2 | 23.0 | 7.5 | 38.7 | 14.2 |
| 113 | 36.6 | — | — | — | — | — | — |
| 114 | — | — | — | — | — | — | — |
| 115 | — | — | — | — | — | — | — |
| 116 | — | — | — | — | — | — | — |
| 117 | 8.4 | — | — | — | 5.7 | — | — |
| 119 | — | — | — | — | — | — | — |
| 120 | 28.6 | — | — | — | — | — | — |
| 121 | — | — | — | — | — | — | — |
| 122 | 31.7 | — | — | — | — | — | — |
| 123 | 44.0 | — | — | — | — | — | — |
| 124 | 4.1 | — | — | — | 8.1 | — | — |
| 125 | — | — | — | — | — | — | — |

TABLE XI-continued

| (1) Test Compound Proc. No. | Bronchodilator/Antiallergy Activity | | | | | | |
|---|---|---|---|---|---|---|---|
| | (2) Spon | (3) Ach | (4) Hist | (5) BaCl₂ | (6) Methacholine Bronchospasm | (7) PCA* | (8) Allergic Bronchospasm |
| | Guinea Pig Trachea | | | | | | |
| 126 | 22.0 | — | — | — | — | — | — |
| 127 | 200 | — | — | — | — | — | — |
| 128 | 100 | — | — | — | — | — | — |

*Compounds were inactive at the oral dose in mg./kg. shown in parentheses after "I".

What is claimed is

1. The method for relieving bronchospasm in a mammal suffering therefrom which comprises administering to said mammal a non-toxic bronchodilator effective dose of a compound selected from the group consisting of

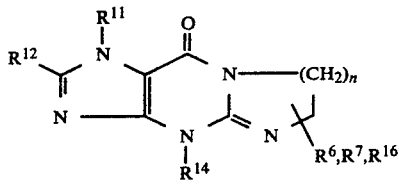

Formula XX' wherein $R^{11}$ is hydrogen or lower alkyl up to 8 carbon atoms, $R^{12}$ is hydrogen, lower alkyl up to 8 carbon atoms or halogen when $R_{11}$ is hydrogen, $R_{14}$ is selected from the group consisting of lower alkyl having up to 8 carbon atoms, cycloalkylalkyl having 4 to 12 carbon atoms, pyridylmethyl, aralkyl or substituted aralkyl having 7 to 12 carbon atoms, aryloxyalkyl or substituted aryloxyalkyl having 8 to 12 carbon atoms wherein each of said substituted aralkyl and substituted aryloxyalkyl groups contains 1 or 2 non-sterically hindered ring substituents selected from halogen and alkoxy having up to 6 carbon atoms, $R^6$ and $R^7$ are attached to ring carbon atoms and are selected from hydrogen, methyl, and ethyl, $R^{16}$ represents hydrogen or a double bond between adjacent ring carbon atoms, n is the integer 1 and the pharmaceutically acceptable acid addition salts thereof.

2. The method for exerting a vasodilator effect in a mammal which comprises administering to a mammal in need of vasodilation a non-toxic vasodilator effective dose of a compound selected from the group consisting of

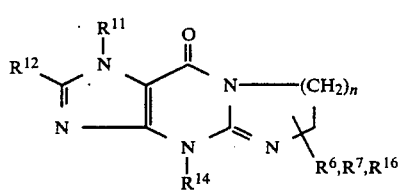

Formula XX' wherein $R^{11}$ is hydrogen or lower alkyl up to 8 carbon atoms, $R^{12}$ is hydrogen, lower alkyl having up to 8 carbon atoms or halogen when $R^{11}$ is hydrogen, $R^{14}$ is selected from the group consisting of lower alkyl having up to 8 carbon atoms, cycloalkylalkyl having 4 to 12 carbon atoms, pyridylmethyl, aralkyl or substituted aralkyl having 7 to 12 carbon atoms, aryloxyalkyl or substituted aryloxyalkyl having 8 to 12 carbon atoms wherein each of said substituted aralkyl and substituted aryloxyalkyl groups contains 1 or 2 non-sterically hindered ring substituents selected from halogen and alkoxy having up to 6 carbon atoms, $R^6$ and $R^7$ are attached to ring carbon atoms and are selected from hydrogen, methyl, and ethyl, $R^{16}$ represents hydrogen or a double bond between adjacent ring carbon atoms, n is the integer 1 and the pharmaceutically acceptable acid additon salts thereof.

3. The method of claims 1 or 2 wherein in said compound $R^{11}$, $R^{12}$, $R^6$, $R^7$, and $R^{16}$ are hydrogen atoms, n is the integer 1, and $R^{14}$ is the substituted aralkyl group.

4. The method of claims 1 or 2 wherein said compound is 4-[(4-chlorophenyl)methyl]-6,7-dihydro-3H-imidazo[1,2-a]purin-9(4H)one.

5. The method of claims 1 or 2 wherein said compound is 4-[(4-chlorophenyl)methyl]-1-6,7-dihydro -3H-imidazo[1,2-a]purin-9(4H)-one hydrochloride.

6. The method of claims 1 or 2 wherein in said compound $R^{11}$ is lower alkyl, $R^{12}$, $R^6$, $R^7$, and $R^{16}$ are hydrogen, n is the integer 1, and $R^{14}$ is the substituted aralkyl group.

7. The method of claims 1 or 2 wherein in said compound $R^{11}$, $R^6$, $R^7$, and $R^{16}$ are hydrogen, $R^{12}$ is alkyl, n is the integer 1, and $R^{14}$ is substituted aralkyl.

8. The method of claims 1 or 2 wherein said compound is 4-[(4-chlorophenyl)methyl]-6,7-dihydro-2-methyl-3H-imidazo[1,2-a]purin-9(4H-one.

9. The method of claims 1 or 2 wherein in said compound $R_{11}$, $R^6$, $R^7$, and $R^{16}$ are hydrogen, $R^{12}$ is halogen, n is the integer 1, and $R^{14}$ is substituted aralkyl.

10. The method of claims 1 or 2 wherein in said compound $R^{11}$, $R^{12}$, $R^6$, $R^7$, and $R^{16}$ are hydrogen, $R^{14}$ is lower alkyl, and n is the integer 1.

11. The method of claims 1 or 2 wherein in said compound $R^{11}$, $R_{12}$, $R^6$, $R^7$, and $R^{16}$ are hydrogen, $R^{14}$ is pyridylmethyl, and n is the integer 1.

12. The method of claims 1 or 2 wherein in said compound $R^{11}$, $R^{12}$, $R^6$, $R^7$, and $R^{16}$ are hydrogen, $R^{14}$ is aralkyl, and n is the integer 1.

13. The method of claims 1 or 2 wherein in said compound $R^{11}$, $R^{12}$, $R^6$, $R^7$, and $R^{16}$ are hydrogen, $R^{14}$ is aryloxyalkyl, and n is the integer 1.

14. The method of claims 1 or 2 wherein said compound is 6,7-dihydro-2-methyl-4-(2-phenoxyethyl) imidazo[1,2-a]purin-9(4H)-one.

15. The method of claims 1 or 2 wherein said compound is 6,7-dihydro-2-methylethyl)-4-(2methylpropyl)-3Himidazo[1,2-a]-purin-9(4H)-one.

16. The method of claims 1 or 2 wherein said compound is 6,7-dihydro-2-methyl-4-(2-methylpropyl)3H-imidazo[1,2-a]purin-9(4H)-one.

17. The method of claims 1 or 2 wherein said compound is 6,7-dihydro-2-(1-methylethyl)-4-(2-phenoxyethyl)-3H-imidazo[1,2-a]purin-9(4H)-one.

18. The method of claims 1 or 2 wherein said compound is 4 [(4-chlorophenyl)methyl]-6,7-dihydro-6-methyl-3H-imidazo[1,2a]purin-9(4H)-one.

19. The method of claims 1 or 2 wherein said compound is 4[-(4-chlorophenyl)methyl]-6,7-dihydro-2,6-dimethyl-3H-imidazo[-1,2-a]-purin-9(4H)-one.

20. The method of claims 1 or 2 wherein said compound is 4[(4-chlorophenyl)methyl]-6,7-dihydro-1,6-dimethyl-1H-imidazo[1,2-a]purin-9(4H-one.

21. The method of claims 1 or 2 wherein said compound is 4-[(4-chlorophenyl)methyl[-6,7-dihydro-1,2,6-trimethyl-1H-imidazo[1,2-a]purin-9(4H-one.

22. The method of claims 1 or 2 wherein said compound is 6,7-dihydro-6-methyl-4-(2-methylpropyl)-3H-imidazo[1,2-a]purin-9(4H)-one.

23. The method of claims 1 or 2 wherein said compound is selected from the group consisting of 4-[(4-chlorophenyl)methyl]-6,7-dihydro-6,6-dimethyl-3H-imidazo]1,2a]purin-9(4H)-one and a pharmaceutically acceptable acid additon salt thereof.

24. The method of claims 1 or 2 wherein said compound is 4-[(4-chlorophenyl)methyl]-6,7-dihydro-6,6-dimethyl-3H-imidazo[1,2-a]purin-9(4H)-one.

25. The method of claims 1 or 2 wherein said compound is 4-[(4-chlorophenyl)methyl]-6,7-dihydro-6,7-dimethyl-3H-imidazo[1,2-a]purin-9(4H)-one.

26. The method of claims 1 or 2 wherein said compound is 4-[(4-chlorophenyl)methyl]-6,7-dihydro-trans-6,7-dimethyl-3H-imidazo[1,2-a]purin-9(4H-one.

27. The method of claims 1 or 2 wherein said compound is 4-[(4-chlorophenyl)methyl]-6,7-dihydro-cis-6,7-dimethyl-3H-imidazo[1,2-a]purin-9(4H)-one.

28. The method of claims 1 or 2 wherein in said compound n is 1, $R^{16}$ is hydrogen, and $R^6$ and $R^7$ are methyl or ethyl.

29. The method of claims 1 or 2 wherein said compound is selected from the group consisting of those having the following formula and the pharmaceutically acceptable acid addition salts thereof

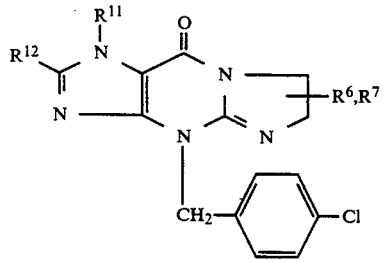

wherein $R^6$, $R^7$, $R^{11}$ and $R^{12}$ are selected from the group consisting of hydrogen and methyl.

30. The method of claims 1 or 2 wherein said compound is selected from the group consisting of those having the following formula and the pharmaceutically acceptable acid addition salts thereof

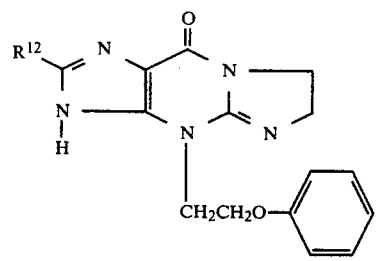

wherein $R^{12}$ is lower alkyl.

31. The method of claims 1 or 2 wherein said compound is selected from the group consisting of those having the following formula and the pharmaceutically acceptable acid addition salts thereof

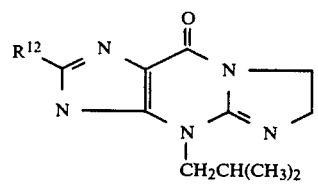

wherein $R^{12}$ is hydrogen or lower alkyl.

32. The method of claim 1 or 2 wherein said compound is selected from the group consisting of
- (a) 4-[(3-chlorophenyl)methyl]-6,7-dihydro-3H-imidazo[1,2-a]purin-9(4H)-one;
- (b) 4-[(2-chlorphenyl)methyl]-6,7-dihydro-3H-imidazo[1,2-a]purin-9(4H)-one;
- (c) 4-[(4-fluorophenyl)methyl]-6,7-dihydro-3H-imidazo[1,2-a]purin-9(4H)-one;
- (d) 4-(2-pyridylmethyl)-6,7-dihydro-3H-imidazo[1,2-a]purin-9(4H)-one;
- (e) 4-[2-(3,4-dimethoxyphenyl)ethyl]-6,7-dihydroxy-3H-imidazo[1,2-a]purin-9(4H)-one;
- (f) 6,7-dihydro-4-(2-phenoxyethyl)-3H-imidazo[1,2a]purin-9(4H)-one;
- (g) 4-[(4-chlorophenyl)methyl]-2-ethyl-6,7-dihydroimidazo[1,2-a]purin-9(4H)-one;
- (h) 2-bromo-4-[(4-chlorophenyl)methyl]-6,7-dihydro-3-H-imidazo[1,2-a]purin-9(4H)-one;
- (i) 6,7-dihydro-2-methyl-4-octyl-3H-imidazo[1,2-a]purin-9(4H)-one;
- (j) 6,7-dihydro-2-(1-methylethyl)-4-octylimidazo[1,2-a]purin-9(4H)-one;
- (k) 4-[2-(4-chlorophenoxy)ethyl]-6,7-dihydro-3H-imidazo[1,2-a]purin-9(4H)-one;
- (l) 4-(cyclohexylmethyl)-6,7-dihydro-3H-imidazo[1,2-a]purin-9(4H)-one; and
- (m) 4-[(4-chlorphenyl)methyl]-6,7-dihydro-1-methyl-1H-imidazo[1,2-a]purin9(4H-one.

* * * * *